United States Patent
Lee et al.

(10) Patent No.: US 9,932,355 B2
(45) Date of Patent: Apr. 3, 2018

(54) 2,5,6,7-TETRASUBSTITUTED THIAZOLO[4,5-B]PYRIDINE DERIVATIVES AND USE THEREOF

(71) Applicant: KYUNGPOOK NATIONAL UNIVERSITY INDUSTRY-ACADEMIC COOPERATION FOUNDATION, Daegu (KR)

(72) Inventors: Taeho Lee, Daegu (KR); Jong-Sup Bae, Daegu (KR); Kyung-Sik Song, Daegu (KR); Sangkyu Lee, Daegu (KR); Kwang-Hyeon Liu, Daegu (KR); Wonhwa Lee, Gyeongsangnam-do (KR); Doohyun Lee, Daegu (KR)

(73) Assignee: KYUNGPOOK NATIONAL UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 14/698,073

(22) Filed: Apr. 28, 2015

(65) Prior Publication Data
US 2015/0307516 A1 Oct. 29, 2015

(30) Foreign Application Priority Data
Apr. 29, 2014 (KR) ........................ 10-2014-0051964

(51) Int. Cl.
*C07D 513/04* (2006.01)

(52) U.S. Cl.
CPC ................................. *C07D 513/04* (2013.01)

(58) Field of Classification Search
CPC ................................................... C07D 513/04
See application file for complete search history.

(56) References Cited

FOREIGN PATENT DOCUMENTS

DE  2722416 A1 * 11/1978 ........... C07C 255/00
EP  2303894 A    12/2009

OTHER PUBLICATIONS

Muller and Kräusslich in "Antiviral Strategies" Handbook of Experimental Pharmacology vol. 189 Chapter 1, pp. 1-24.*
Gentile "HMGB1 as a therapeutic target for sepsis: it's all in the timing!" Expert Opinion on Therapeutic Targets, 2014 18:3, 243-245.*
Marshall "Why have clinical trials in sepsis failed?" Trends in Molecular Medicine, Apr. 2014, vol. 20, No. 4 195-203.*
Garrido "Experimental models of sepsis and septic shock: an overview" Acta Cirúrgica Brasileira—vol. 19 (2) 2004 82-88.*
Poli-de-Figueiredo "Experimental Models of Sepsis and Their Clinical Relevance" Shock, vol. 30, Supplement 1, pp. 53-59, 2008.*
Lee, et al., "Solid-Phase Synthesis of Thiazolo[4,5-b]pyridine Derivatives Using Friedländer Reaction," *Journal of Combinatorial Chemistry*, 2010, 12(1):95-99.
Andersson et al., 2011, "HMGB1 Is a Therapeutic Target for Sterile Inflammation and Infection," Annu. Rev. Immunol., 29:139-62.
Bae et al., 2011, "Activated protein C inhibits high mobility group box 1 signaling in endothelial cells," Blood, 118:3952-3959.
Fink et al., 2007, "Bench-to-bedside review: High-mobility group box 1 and critical illness," Critical Care, 11:229.
Gibot et al., 2007, "High-mobility group box 1 protein plasma concentrations during septic shock," Intensive Care Med, 33:1347-1353.
Hori et al., 1995, "The Receptor for Advanced Glycation End Products (RAGE) Is a Cellular Binding Site for Amphoterin," The Journal of Biological Chemistry, 270(43):25752-25761.
Park et al., 2004, "Involvement of Toll-like Receptors 2 and 4 in Cellular Activation by High Mobility Group Box 1 Protein," The Journal of Biological Chemistry, 279(9):7370-7377.
Sundén-Cullberg et al., 2005, "Persistent elevation of high mobility group box-1 protein (HMGB1) in patients with severe sepsis and septic shock," Crit Care Med, 33(3):564-573.
Wang et al., 2004, "Extracellular role of HMGB1 in inflammation and sepsis," Journal of Internal Medicine, 255:320-331.
Wang et al., 2004, "Cholinergic agonists inhibit HMGB1 release and improve survival in experimental sepsis," Nat Med, 10(11):1216-1221.
Yang et al., 2006, "Anti-HMGB1 Neutralizing Antibody Ameliorates Gut Barrier Dysfunction and Improves Survival after Hemorrhagic Shock," Mol Med, 12(4-6):105-114.
Yang et al., 2010, "A critical cysteine is required for HMGB1 binding to Toll-like receptor 4 and activation of macrophage cytokine release," PNAS, 107(26):11942-11947.

* cited by examiner

*Primary Examiner* — David K O'Dell
(74) *Attorney, Agent, or Firm* — Riverside Law LLP

(57) ABSTRACT

Provided are a pharmaceutical composition containing a 2,5,6,7-tetrasubstituted thiazolo[4,5-b]pyridine derivative represented by Formula 1 as an active ingredient and a use thereof effective on a vascular inflammation-related infectious disease triggered by activity of HMGB1 protein. As investigating an anti-sepsis effect through a CLP-induced sepsis animal test that a sepsis survival rate is increased, it is identified that the pharmaceutical composition contains the 2,5,6,7-tetrasubstituted thiazolo[4,5-b]pyridine derivative or a pharmaceutically available salt thereof as an active ingredient to be used as a therapeutic agent for a vascular inflammatory disease and infectious disease including sepsis triggered by activity of HMGB1 protein.

3 Claims, 1 Drawing Sheet

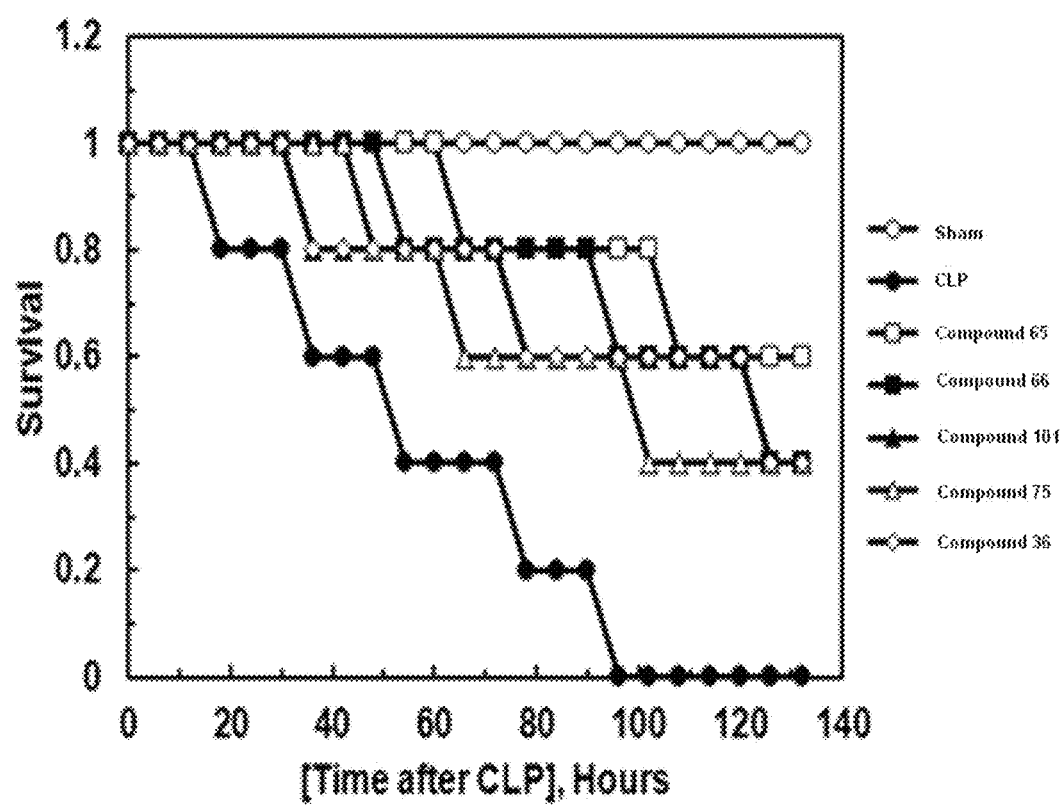

2,5,6,7-TETRASUBSTITUTED THIAZOLO[4,5-B]PYRIDINE DERIVATIVES AND USE THEREOF

CROSS-REFERENCE TO RELATED APPLICATION

This application claims priority to and the benefit of Korean Patent Application No. 2014-0051964, filed on Apr. 29, 2014, the disclosure of which is incorporated herein by reference in its entirety.

BACKGROUND

1. Field of the Invention

The present invention relates to a 2,5,6,7-tetrasubstituted thiazolo[4,5-b]pyridine derivative and a use thereof. More particularly, the present invention relates to a 2,5,6,7-tetrasubstituted thiazolo[4,5-b]pyridine derivative and a pharmaceutically available salt thereof as a new compound exhibiting an inhibitory activity against various types of inflammation mediated by HMGB1 protein, and a pharmaceutical composition for preventing or treating a vascular inflammatory disease and infectious disease, which contains the derivative as an active ingredient.

2. Discussion of Related Art

Sepsis refers to systemic infection occurring when germs penetrate into a blood, and a fatal diseases since over 225,000 of people die of sepsis yearly only in the United State. Even though the cause of the disease is simple, the sepsis includes various ranges of inflammation mechanisms. Due to such complexity, Xirgis was approved by FDA in 2001 as the only drug for treating sepsis after more than 20 years of research. However, on October, 2011, because of the question on efficacy for the treatment of sepsis, Xigris disappeared from the market, and since then, there has not been an apparent drug.

First, in the 'Proceedings of the National Academy of Sciences', it is disclosed by Tracey et al. that a transcription factor, high-mobility group box 1 (HMGB1), induces a cytokine reaction of a host cell to bacteriotoxin, and thus research on HMGB1 as a target protein for treating sepsis started [Yang H, PNAS, 2010, 107, 11942-11947]. HMGB1 is known as a DNA binding protein to induce inflammation [Fink M P, Critical care, 2007, 11:229]. When cell death or necrosis occurs in immunocytes or non-immunocytes, HMGB1 is secreted [Anderson U, Annu. Rev. immunol., 2011, 29, 139-162]. Sepsis occurs by inducing attachment and transfer of immunocytes by increasing permeability of vein endothelial cells by HMGB1 secreted into a blood [Bae J S, Blood, 2011, 118, 3952-3959]. In macrophages and vein endothelial cells, HMGB1 binds to Toll like receptor-2, 4 (TLR-2, 4) or Receptor for the advanced glycation end products (RAGEs), thereby secreting TNF-alpha and IL-6, and NF-kB and ERK-1/2 are activated, leading to serious vascular inflammation [Hori O, J. Biol. Chem., 270, 25752-25761, Park J S, J. Biol. Chem., 2004, 279, 7370-7377].

It was found that at the 18 hours after cecal ligation and puncture (CLP) surgery using a CLP surgery mouse model having the highest relevance with sepsis, an HMGB1 level is largely increased, and thus a clinical symptom of the sepsis is developed [Wang H, J. Internal Med., 2004, 255, 320-331]. Afterward, when an antibody with respect to HMGB1 was administered at 24 hours, a survival rate was highly increased, and the approach was remarkable as the first cytokine treatment method effective even when after the antibody was administered at 8 hours after the CLP treatment [Wang H, Nat. Med. 2004, 10, 1216-1221]. Accordingly, an organ damage was prevented in an animal treated with an HMGB1 inhibitor, and a protective action against death was maintained [Wang H, Nat. Med. 2004, 10, 1216-1221]. A clinical research result in which HMGB1 is secreted from cells and exists in a plasma in a patient of trauma or sepsis was reported [Yang R, Molecular medicine, 2006, 12, 105-114]. It was confirmed that HMGB1 was increased in a plasma within the first week after diagnosis in most of sepsis or septic shock patients, and an organ damage caused by systemic inflammation was observed [Gibot S, Intensive Care Med, 2007, 33, 1347-1353, Sunden-Cullberg J, Crit. Care Med., 2005, 33, 564-573]. Based on such a research result, a vascular inflammatory disease and infectious disease including sepsis can be prevented or treated through regulation of an activity of HMGB1 protein.

Therefore, as the result of investigating a new compound which can be applied as a drug for treating vascular inflammation, the inventors designed and synthesized a 2,5,6,7-tetrasubstituted thiazolo[4,5-b]pyridine derivative compound, and conducted a CLP-induced sepsis animal test using the prepared 2,5,6,7-tetrasubstituted thiazolo[4,5-b]pyridine derivative compound from understanding that an effect of inhibiting an activity of the HMGB1 protein has not been reported, thereby confirming that an excellent sepsis survival rate was obtained, and thus completed the present invention.

SUMMARY OF THE INVENTION

The present invention is directed to providing a 2,5,6,7-tetrasubstituted thiazolo[4,5-b]pyridine derivative compound and a pharmaceutically available salt thereof.

The present invention is also directed to providing a pharmaceutical composition for preventing or treating a vascular inflammatory disease and infectious disease using an effect of inhibiting an activity of HMGB1 protein, which contains a 2,5,6,7-tetrasubstituted thiazolo[4,5-b]pyridine derivative compound or a pharmaceutically available salt thereof as an active ingredient.

However, technical objects to be achieved by the present invention are not limited to the above descriptions, and other objects not described will be clearly understood to those of ordinary skill in the art from the following descriptions.

In one aspect of the present invention, the present invention provides a 2,5,6,7-tetrasubstituted thiazolo[4,5-b]pyridine derivative represented by Formula 1 and a pharmaceutically available salt thereof

[Formula 1]

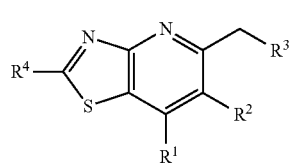

In Formula 1, $R^1$ is a five to seven-membered substituted or unsubstituted aromatic group to which carbon, oxygen, nitrogen or sulfur is added. Here, the aromatic group is a heteroaryl group, a phenyl group or a substituted phenyl group, here, the substituent is one to four substituents selected from the group consisting of hydrogen, halogen, cyano, nitro, hydroxy, $C_1$~$C_{10}$ linear or branched alkyl, $C_1$~$C_{10}$ alkoxy, $C_1$~$C_{10}$ haloalkyl, $C_1$~$C_{10}$ haloalkoxy, $C_1$~$C_{10}$ alkylthio, $C_1$~$C_{10}$ alkyl carbonyl and a $C_1$~$C_{10}$ alkoxy carbonyl group, $R^2$ and $R^3$ are hydrogen, a $C_1$~$C_{10}$ linear, branched or cyclic alkyl group, a cyclic $C_1$~$C_{10}$ alkyl group including a heteroelement (—NH—, —S—, —O—) or heteroalkyl group, or a $C_1$~$C_{10}$ linear or branched carbonyl group, which are independently or identically substituted, and $R^4$ is an amino group substituted by one or at least two $C_1$~$C_{10}$ linear, branched or cyclic alkyl groups, $C_5$~$C_{10}$ aryl groups, $C_5$~$C_{10}$ heteroaryl groups or substituted heteroaryl groups, $C_5$~$C_{10}$ arylalkyl groups, a benzyl group, a substituted benzyl group or $C_5$~$C_{10}$ heteroarylalkyl groups, or a phenyl group, a substituted phenyl group, a benzyl group, a substituted benzyl group, a $C_1$~$C_{10}$ linear, branched or cyclic alkyl group, or an amine group having a piperazine

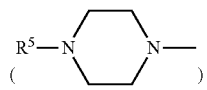

substituted by phenyl or a heteroarylamide group, or a $C_3$~$C_{10}$ cyclic amine group, or a $C_3$~$C_{10}$ cyclic amine group containing at least one heteroatom selected from the group consisting of N, O, and S, here, the substituent is one to three substituents selected from the group consisting of a halogen atom, a nitro group, a $C_1$~$C_{10}$ alkyl group, a $C_1$~$C_{10}$ alkoxy group, a $C_1$~$C_{10}$ haloalkyl group and a $C_1$~$C_{10}$ haloalkoxy group.

In one exemplary embodiment of the present invention, in Formula 1, $R^1$ is a five to seven-membered substituted or unsubstituted aromatic group to which carbon, oxygen, nitrogen or sulfur is added, in which the aromatic group is a furanyl group, a thiophenyl group, a phenyl group, a thiazole group, an indole group, an isoindole group, a pyridinyl group, a piperazinyl group, a pyridazinyl group, a naphthyl group, a quinolinyl group, or an isoquinolinyl group, here, the substituent includes one to three substituents selected from the group consisting of hydrogen, halogen, cyano, nitro, hydroxy, $C_1$~$C_6$ linear or branched alkyl, $C_1$~$C_6$ alkoxy, $C_1$~$C_6$ haloalkyl, $C_1$~$C_6$ haloalkoxy, alkylthio, $C_1$~$C_6$ alkyl carbonyl and a $C_1$~$C_6$ alkoxy carbonyl group, $R^2$ and $R^3$ are hydrogen, a $C_1$~$C_6$ linear, branched or cyclic alkyl group, a cyclic $C_1$~$C_6$ alkyl group including a heteroelement (—NH—, —S—, —O—) or heteroalkyl group, or a $C_1$~$C_6$ linear or branched carbonyl group, which are independently or identically substituted, and $R^4$ is an amino group substituted by one or at least two $C_1$~$C_6$ linear, branched or cyclic alkyl groups, $C_5$~$C_6$ aryl groups, $C_5$~$C_6$ heteroaryl groups or substituted heteroaryl groups, $C_5$~$C_6$ arylalkyl groups, a benzyl group, a substituted benzyl group or $C_5$~$C_6$ heteroarylalkyl groups, or a phenyl group, a substituted phenyl group, a benzyl group, a substituted benzyl group, a $C_1$~$C_6$ linear, branched or cyclic alkyl group, or an amine group having a piperazine

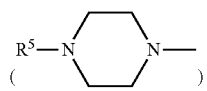

substituted by phenyl or a heteroarylamide group, or a $C_3$~$C_6$ cyclic amine group, or a $C_3$~$C_6$ cyclic amine group containing at least one heteroatom selected from the group consisting of N, O, and S, here, the substituent is one to three substituents selected from the group consisting of a halogen atom, a nitro group, a $C_1$~$C_6$ alkyl group, a $C_1$~$C_6$ alkoxy group, a $C_1$~$C_6$ haloalkyl group and a $C_1$~$C_6$ haloalkoxy group.

In another exemplary embodiment of the present invention, in Formula 1, $R^1$ is a phenyl group, a substituted phenyl group, an aryl group, or a substituted aryl group, in which the aryl group is a furanyl group, a thiophenyl group, a thiazole group, an indole group, an isoindole group, a pyridinyl group, a piperazinyl group, a pyridazinyl group, a naphthyl group, a quinolinyl group, an isoquinolinyl group, here, the substituent includes one to three substituents selected from the group consisting of hydrogen, chloro, fluoro, a hydroxyl group, a cyano group, a nitro group, a methyl group, an ethyl group, an isopropyl group, a cyclopropyl group, a t-butyl group, a methoxy group, an ethoxy group, an n-propoxy group, an isopropoxy group, a thiomethoxy group, a thioethoxy group, a thio n-propoxy group, a thio isopropoxy group, a trifluoromethoxy group, a trifluoromethyl group, a methylester group, and an ethylester group, $R^2$ and $R^3$ are independently hydrogen, methyl, ethyl, n-propyl, butyl, an isopropyl group, or identically cyclopentyl, cyclohexyl, cycloheptyl, cyclopentanone, cyclohexanone, cycloheptanone, tetrahydropyran, tetrahydrothiopyran or piperidine, and $R^4$ is an amino group substituted by one or at least two $C_1$~$C_6$ linear, branched or cyclic alkyl groups, $C_5$~$C_6$ aryl groups, $C_5$~$C_6$ heteroaryl groups or substituted heteroaryl groups, $C_5$~$C_6$ arylalkyl groups, a benzyl group or $C_5$~$C_6$ heteroarylalkyl groups, or a phenyl group, a substituted phenyl group, a benzyl group, a substituted benzyl group, a $C_1$~$C_{10}$ linear, branched or cyclic alkyl group, or a $C_3$~$C_6$ cyclic amine group, or a $C_3$~$C_6$ cyclic amine group containing at least one heteroatom selected from the group consisting of N, O, and S, here, the substituent is one to three substituents selected from the group consisting of a halogen atom, a nitro group, a $C_1$~$C_4$ alkyl group, a alkoxy group, a $C_1$~$C_3$ haloalkyl group and a $C_1$~$C_3$ haloalkoxy group.

In still another exemplary embodiment of the present invention, the 2,5,6,7-tetrasubstituted thiazolo[4,5-b]pyridine derivative is any one selected from the group consisting of 9-phenyl-N-propyl-5,6,7,8-tetrahydrothiazolo[4,5-b]quinoline-2-amine, 10-phenyl-N-propyl-6,7,8,9-tetrahydro-5H-cyclohepta[b]thiazolo[5,4-e]pyridine-2-amine, 2-(4-methoxybenzylamino)-9-phenyl-6,7-dihydrothiazolo[4,5-b]quinoline-8(5H)-one, N-benzyl-9-(4-methoxyphenyl)-5,6,7,8-tetrahydrothiazolo[4,5-b]quinoline-2-amine, 4-(9-(4-methoxyphenyl)-5,6,7,8-tetrahydrothiazolo[4,5-b]quinoline-2-yl)morpholine, 9-(4-methoxyphenyl)-2-(piperidine-1-yl)-5,6,7,8-tetrahydrothiazolo[4,5-b]quinoline, (4-methoxybenzyl)-9-(4-methoxyphenyl)-5,6,7,8-tetrahydrothiazolo[4,5-b]quinoline-2-amine, 9-(4-methoxyphenyl)-N-propyl-5,6,7,8-tetrahydrothiazolo[4,5-b]quinoline-2-amine, 9-(4-methoxyphenyl)-2-(pyrrolidine-1-yl)-5,6,7,8-tetrahydrothiazolo[4,5-b]quinoline, 10-(4-methoxyphenyl)-N-propyl-6,7,8,9-tetrahydro-5H-cyclohepta[b]thiazolo[5,4-e]pyridine-2-amine, 10-(4-methoxyphenyl)-2-(pyrrolidine-1-yl)-6,7,8,9-tetrahydro-5H-cyclohepta[b]thiazolo[5,4-e]pyridine, and 9-(4-nitrophenyl)-2-(pyrrolidine-1-yl)-5,6,7,8-tetrahydrothiazolo[4,5-b]quinoline.

Another aspect of the present invention provides a pharmaceutical composition for preventing or treating a vascular inflammatory disease and infectious disease, which contains the 2,5,6,7-tetrasubstituted thiazolo[4,5-b]pyridine derivative represented by Formula 1 or a pharmaceutically available salt thereof as an active ingredient.

In one exemplary embodiment of the present invention, the vascular inflammatory disease and infectious disease include sepsis.

In another exemplary embodiment of the present invention, the composition inhibits an activity of HMGB1 protein.

Still another aspect of the present invention provides a method of treating a vascular inflammatory disease and infectious disease, which includes administering the pharmaceutical composition to an individual.

Yet another aspect of the present invention provides a method of using the pharmaceutical composition to prevent or treat a vascular inflammatory disease and infectious disease.

BRIEF DESCRIPTION OF THE DRAWINGS

The above and other objects, features, and advantages of the present invention will become more apparent to those of ordinary skill in the art by describing exemplary embodiments thereof in detail with reference to the accompanying drawings, in which:

FIG. 1 is a graph showing a survival rate of a CLP-induced sepsis mouse model after administration of compounds 1-36, 1-65, 1-66, 1-75, and 1-101.

DETAILED DESCRIPTION OF EXEMPLARY EMBODIMENTS

The present invention provides a 2,5,6,7-tetrasubstituted thiazolo[4,5-b]pyridine derivative represented by Formula 1 and a pharmaceutically available salt thereof.

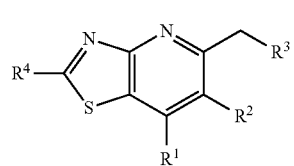

[Formula 1]

In Formula 1, $R^1$ is a five to seven-membered substituted or unsubstituted aromatic group to which carbon, oxygen, nitrogen or sulfur is added. Here, the aromatic group is a heteroaryl group, a phenyl group or a substituted phenyl group, here, the substituent includes one to four substituents selected from the group consisting of hydrogen, halogen, cyano, nitro, hydroxy, $C_1$~$C_{10}$ linear or branched alkyl, $C_1$~$C_{10}$ alkoxy, $C_1$~$C_{10}$ haloalkyl, $C_1$~$C_{10}$ haloalkoxy, $C_1$~$C_{10}$ alkylthio, $C_1$~$C_{10}$ alkyl carbonyl and a $C_1$~$C_{10}$ alkoxy carbonyl group, $R^2$ and $R^3$ are hydrogen, a $C_1$~$C_{10}$ linear, branched or cyclic alkyl group, a cyclic $C_1$~$C_{10}$ alkyl group including a heteroelement (—NH—, —S—, —O—) or heteroalkyl group, or a $C_1$~$C_{10}$ linear or branched carbonyl group, which are independently or identically substituted, and $R^4$ is an amino group substituted by one or at least two $C_1$~$C_{10}$ linear, branched or cyclic alkyl groups, $C_5$~$C_{10}$ aryl groups, $C_5$~$C_{10}$ heteroaryl groups or substituted heteroaryl groups, $C_5$~$C_{10}$ arylalkyl groups, a benzyl group, a substituted benzyl group or $C_5$~$C_{10}$ heteroarylalkyl groups, or a phenyl group, a substituted phenyl group, a benzyl group, a substituted benzyl group, a $C_1$~$C_{10}$ linear, branched or cyclic alkyl group, or an amine group having a piperazine

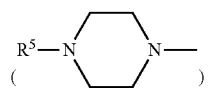

substituted by phenyl or a heteroarylamide group, or a $C_3$~$C_{10}$ cyclic amine group, or a $C_3$~$C_{10}$ cyclic amine group containing at least one heteroatom selected from the group consisting of N, O, and S, here, the substituent is one to three substituents selected from the group consisting of a halogen atom, a nitro group, a $C_1$~$C_{10}$ alkyl group, a $C_1$~$C_{10}$ alkoxy group, a $C_1$~$C_{10}$ haloalkyl group and a $C_1$~$C_{10}$ haloalkoxy group.

A preferable example of the 2,5,6,7-tetrasubstituted thiazolo[4,5-b]pyridine derivative represented by Formula 1 according to the present invention is as follows:

In the 2,5,6,7-tetrasubstituted thiazolo[4,5-b]pyridine derivative, $R^1$ is a five to seven-membered substituted or unsubstituted aromatic group to which carbon, oxygen, nitrogen or sulfur is added, in which the aromatic group is a furanyl group, a thiophenyl group, a phenyl group, a thiazole group, an indole group, an isoindole group, a pyridinyl group, a piperazinyl group, a pyridazinyl group, a naphthyl group, a quinolinyl group, or an isoquinolinyl group, here, the substituent includes one to three substituents selected from the group consisting of hydrogen, halogen, cyano, nitro, hydroxy, $C_1$~$C_6$ linear or branched alkyl, $C_1$~$C_6$ alkoxy, $C_1$~$C_6$ haloalkyl, $C_1$~$C_6$ haloalkoxy, $C_1$~$C_6$ alkylthio, $C_1$~$C_6$ alkyl carbonyl and a $C_1$~$C_6$ alkoxy carbonyl group, $R^2$ and $R^3$ are hydrogen, a $C_1$~$C_6$ linear, branched or cyclic alkyl group, a cyclic $C_1$~$C_6$ alkyl group including a heteroelement (—NH—, —S—, —O—) or heteroalkyl group, or a $C_1$~$C_6$ linear or branched carbonyl group, which are independently or identically substituted, and $R^4$ is an amino group substituted by one or at least two $C_1$~$C_6$ linear, branched or cyclic alkyl groups, $C_5$~$C_6$ aryl groups, $C_5$~$C_6$ heteroaryl groups or substituted heteroaryl groups, $C_5$~$C_6$ arylalkyl groups, a benzyl group, a substituted benzyl group or $C_5$~$C_6$ heteroarylalkyl groups, or a phenyl group, a substituted phenyl group, a benzyl group, a substituted benzyl group, a $C_1$~$C_6$ linear, branched or cyclic alkyl group, or an amine group having a piperazine

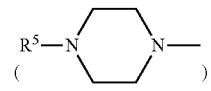

substituted by phenyl or a heteroarylamide group, or a $C_3$~$C_6$ cyclic amine group, or a $C_3$~$C_6$ cyclic amine group containing at least one heteroatom selected from the group consisting of N, O, and S, here, the substituent is one to three substituents selected from the group consisting of a halogen atom, a nitro group, a $C_1$~$C_6$ alkyl group, a $C_1$~$C_6$ alkoxy group, a $C_1$~$C_6$ haloalkyl group and a $C_1$~$C_6$ haloalkoxy group.

In the 2,5,6,7-tetrasubstituted thiazolo[4,5-b]pyridine derivative, $R^1$ is a phenyl group, a substituted phenyl group, an aryl group, or a substituted aryl group, in which the aryl group is a furanyl group, a thiophenyl group, a thiazole group, an indole group, an isoindole group, a pyridinyl group, a piperazinyl group, a pyridazinyl group, a naphthyl group, a quinolinyl group, or an isoquinolinyl group, here, the substituent includes one to three substituents selected from the group consisting of hydrogen, chloro, fluoro, a hydroxyl group, a cyano group, a nitro group, a methyl group, an ethyl group, an isopropyl group, a cyclopropyl group, a t-butyl group, a methoxy group, an ethoxy group, an n-propoxy group, an isopropoxy group, a thiomethoxy group, a thioethoxy group, a thio n-propoxy group, a thio isopropoxy group, a trifluoromethoxy group, a trifluoromethyl group, a methylester group, and an ethylester group, $R^2$ and $R^3$ are independently hydrogen, methyl, ethyl, n-propyl, butyl, an isopropyl group, or identically cyclopentyl, cyclohexyl, cycloheptyl, cyclopentanone, cyclohexanone, cycloheptanone, tetrahydropyran, tetrahydrothiopyran or piperidine, and $R^4$ is an amino group substituted by one or at least two $C_1$~$C_6$ linear, branched or cyclic alkyl groups, $C_5$~$C_6$ aryl groups, $C_5$~$C_6$ heteroaryl groups or substituted heteroaryl groups, $C_5$~$C_6$ arylalkyl groups, a benzyl group or $C_5$~$C_6$ heteroarylalkyl groups, or a phenyl group, a substituted phenyl group, a benzyl group, a substituted benzyl group, a $C_1$~$C_{10}$ linear, branched or cyclic alkyl group, or a $C_3$~$C_6$ cyclic amine group, or a $C_3$~$C_6$ cyclic amine group containing at least one heteroatom selected from the group consisting of N, O, and S, here, the substituent is one to three substituents selected from the group consisting of a halogen atom, a nitro group, a $C_1$~$C_4$ alkyl group, a $C_1$~$C_4$ alkoxy group, a $C_1$~$C_3$ haloalkyl group and a $C_1$~$C_3$ haloalkoxy group.

In addition, a more preferable example of the 2,5,6,7-tetrasubstituted thiazolo[4,5-b]pyridine derivative represented by Formula 1 is as follows:
9-phenyl-N-propyl-5,6,7,8-tetrahydrothiazolo[4,5-b]quinoline-2-amine, 10-phenyl-N-propyl-6,7,8,9-tetrahydro-5H-cyclohepta[b]thiazolo[5,4-e]pyridine-2-amine, 2-(4-methoxybenzylamino)-9-phenyl-6,7-dihydrothiazolo[4,5-b]quinoline-8(5H)-one, N-benzyl-9-(4-methoxyphenyl)-5,6,7,8-tetrahydrothiazolo[4,5-b]quinoline-2-amine, 4-(9-(4-methoxyphenyl)-5,6,7,8-tetrahydrothiazolo[4,5-b]quinoline-2-yl)morpholine, 9-(4-methoxyphenyl)-2-(piperidine-1-yl)-5,6,7,8-tetrahydrothiazolo[4,5-b]quinoline, N-(4-methoxybenzyl)-9-(4-methoxyphenyl)-5,6,7,8-tetrahydrothiazolo[4,5-b]quinoline-2-amine, 9-(4-methoxyphenyl)-N-propyl-5,6,7,8-tetrahydrothiazolo[4,5-b]quinoline-2-amine, 9-(4-methoxyphenyl)-2-(pyrrolidine-1-yl)-5,6,7,8-tetrahydrothiazolo[4,5-b]quinoline, 10-(4-methoxyphenyl)-N-propyl-6,7,8,9-tetrahydro-5H-cyclohepta[b]thiazolo[5,4-e]pyridine-2-amine, 10-(4-methoxyphenyl)-2-(pyrrolidine-1-yl)-6,7,8,9-tetrahydro-5H-cyclohepta[b]thiazolo[5,4-e]pyridine, or 9-(4-nitrophenyl)-2-(pyrrolidine-1-yl)-5,6,7,8-tetrahydrothiazolo[4,5-b]quinoline.

The term "pharmaceutically available salt thereof" used herein may be prepared by a conventional method used in the art, and forms a salt of an inorganic acid such as hydrochloric acid, hydrogen bromide, sulfuric acid, hydrogen sodium sulfate, phosphoric acid, carbonic acid, etc. or a pharmaceutically available salt of an acid thereof with an organic acid such as formic acid, acetic acid, oxalic acid, benzoic acid, citric acid, tartaric acid, gluconic acid, gestisic acid, fumaric acid, lactobionic acid, salicylic acid, or acetylsalicylic acid (aspirin), or forms a metal salt thereof by a reaction with an alkali metal ion such as sodium or potassium, or forms a different type of pharmaceutically available salt thereof by a reaction with an ammonium ion.

According to an exemplary embodiment of the present invention, vascular permeation inhibiting performance of the prepared compounds was confirmed using a transwell plate (Cornig, 3462) (Example 3), and anti-inflammation efficacy of the prepared compound was confirmed using a survival rate of peritonitis-induced sepsis mouse model (Example 4). Therefore, the 2,5,6,7-tetrasubstituted thiazolo[4,5-b]pyridine derivative of the present invention and the pharmaceutically available salt thereof may be used to prevent or treat a vascular inflammatory disease.

Accordingly, the present invention provides a pharmaceutical composition for preventing or treating a vascular inflammatory disease and infectious disease, which contains a 2,5,6,7-tetrasubstituted thiazolo[4,5-b]pyridine derivative or a pharmaceutically available salt thereof as an active ingredient.

The term "prevention" used herein refers to all types of behaviors inhibiting vascular inflammation or delaying the occurrence of a disease by administration of the pharmaceutical composition according to the present invention.

The term "treatment" used herein refers to all types of behaviors improving or altering for the better by administration of the pharmaceutical composition according to the present invention.

The term "individual" used herein refers to an object having a disease that needs to be treated, and more particularly, a mammal such as a human, or a non-human mammal such as a primate, a mouse, a rat, a dog, a cat, a horse or a cow.

In the present invention, the vascular inflammation and injection may be, but is not limited to, atherosclerosis or vasculitis, and preferably sepsis.

The pharmaceutical composition of the present invention may contain a 2,5,6,7-tetrasubstituted thiazolo[4,5-b]pyridine derivative represented by Formula 1, a pharmaceutically available salt thereof, a solubilized product thereof, or a hydrate thereof as an active ingredient, and may be prepared as a conventional preparation in a pharmaceutical field, for example, a preparation for oral administration or a preparation for parenteral administration such as a tablet, a capsule, a troche, a liquid or a suspension by adding conventional non-toxic pharmaceutically available carrier, reinforcing agent and excipient to the active ingredient.

As the excipient that can be used in the pharmaceutical composition of the present invention, a sweetener, a binder, a solubilizer, a solubilizing agent, a wetting agent, an emulsifier, an isotonic agent, an adsorption agent, a disintegrating agent, an antioxidant, a preservative, a lubricant, a filler, or a flavoring agent may be included. For example, the excipient may be lactose, dextrose, sucrose, mannitol, sorbitol, cellulose, glycine, silica, talc, stearic acid, sterin, magnesium stearate, magnesium aluminum silicate, starch, gelatin, tragacanth gum, alginic acid, sodium alginate, methyl cellulose, sodium carboxylmethylcellulose, agar, water, ethanol, polyethyleneglycol, polyvinylpyrrolidone, sodium chloride, calcium chloride, orange essence, strawberry essence, or vanilla flavor.

The pharmaceutical composition according to the present invention is administered at a pharmaceutically effective amount. The "pharmaceutically effective amount" used herein refers to an amount sufficient to treat a disease in a reasonable benefit/risk ratio applicable to medical treatment, and the effective level may be determined according to factors including a type of a disease, severity, an activity of a disease, sensitivity to a drug, an administration time, an administration route, an excretion ratio, and a treatment period of a patient, and a co-used drug, and other factors known in the medical field. The pharmaceutical composition according to the present invention may be administered alone or in combination with another therapeutic agent, and sequentially or simultaneously administered with the conventional therapeutic agent once or several times. It is important that the composition is administered at a minimum amount capable of obtain the maximum effect without side effects in consideration of all of the factors, and the amount may be easily determined by those of ordinary skill in the art.

Specifically, the effective amount of the pharmaceutical composition according to the present invention may be changed according to a patient's age, sex, condition and weight, an absorption degree of an active ingredient in vivo, an inactivating rate and an excretion rate, a type of a disease, and a co-used drug, generally, may be 0.1 to 100 mg/kg, and preferably 1 to 30 mg/kg a day. The pharmaceutical composition may be administered once or several times a day.

The pharmaceutical composition of the present invention may be administered to an individual in various routes. All types of administration may be expected, and for example, the pharmaceutical composition may be administered in a route of oral administration, rectal administration, or intravenous, intramuscular, subcutaneous, endometrial or cerebrovascular injection. The pharmaceutical composition of the present invention is determined by a type of a drug, which is an active ingredient, as well as various related factors such as a disease to be treated, an administration route, an age, sex and weight of a patient, and severity of a disease.

In addition, to prevent and treat a vascular inflammatory disease and infectious disease, the pharmaceutical composition of the present invention may be used alone, or in combination with methods using surgery, hormone therapy, drug therapy and a biological reaction regulator.

The present invention provides a method of preparing the 2,5,6,7-tetrasubstituted thiazolo[4,5-b]pyridine derivative represented by Formula 1.

The preparation method of the present invention is simply shown in Reaction Scheme 1.

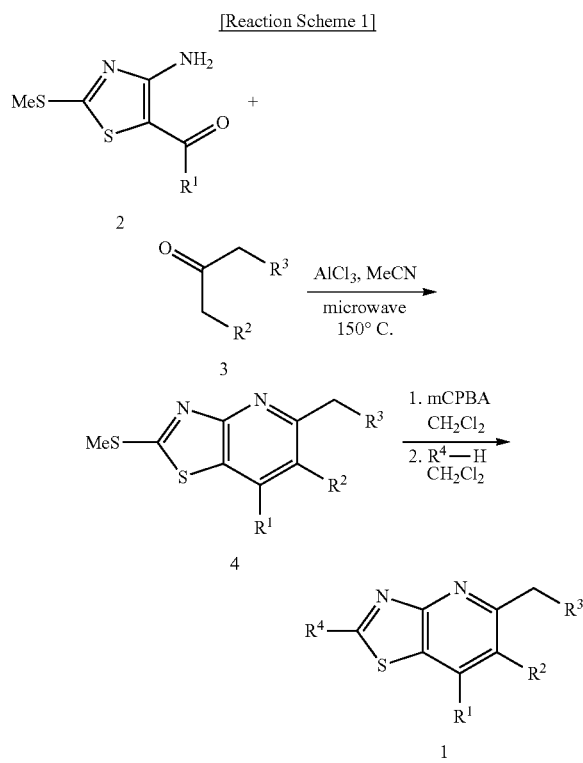

[Reaction Scheme 1]

(In Reaction Scheme 1, $R^1$, $R^2$, $R^3$ and $R^4$ are described as above.)

More particularly, the method includes: a first operation of synthesizing a thiazolo[4,5-b]pyridine intermediate represented by Formula 4 by a condensation reaction between an $R^1$-substituted aminothiazole compound represented by Formula 2, which can be conventionally obtained, and an $R^2$ and $R^3$-substituted ketone represented by Formula 3, which can be commercially available; and a second operation of synthesizing the $R^1$, $R^2$, $R^3$, and $R^4$-introduced 2,5,6,7-tetrasubstituted thiazolo[4,5-b]pyridine derivative compound represented by Formula 1 by a reaction between the thiazolo[4,5-b]pyridine intermediate represented by Formula 4 and an $R^4$—H compound serving as a nucleophile.

Ranges of choices of a reaction process, a solvent-based composition and a reaction condition according to the present invention will be described in further detail below.

In the first operation, the reaction of synthesizing the thiazolo[4,5-b]pyridine intermediate represented by Formula 4 uses acetonitrile (MeCN), toluene, dichloroethane ($ClCH_2CH_2Cl$), dioxane, tetrahydrofuran (THF), N,N-dimethylformamide (DMF), N,N-dimethylacetamide (DMA), or dimethylsulfoxide (DMSO), and preferably acetonitrile as a solvent. The $R^2$ and $R^3$-substituted ketone is used in this reaction at 1 to 5 equivalents, and preferably, 1 and 2 equivalents, with respect to the $R^1$-substituted aminothiazole compound represented by Formula 2 for excellent economic feasibility. Here, as an acid or reagent, trichloroaluminum, p-toluene sulfonic acid, camphorsulfonic acid, N,N-diisopropylethylamine, triethylamine ($Et_3N$), trichloroferrate, or bromolithium may be representatively used, and trichloroaluminum is preferably used. In addition, heating using a microwave is performed under a condition corresponding to a boiling point of the solvent, and preferably, 150° C. In addition, here, the used $R^2$ and $R^3$ substituents may be alkyl halides including the above-described materials.

In the second operation, the reaction of oxidizing a sulfide into a sulfone may use dichloromethane ($CH_2Cl_2$), acetonitrile (MeCN), dichloroethane ($ClCH_2CH_2Cl$), dioxane, or tetrahydrofuran (THF), and preferably, dichloromethane, as a solvent. An oxidant used in this reaction is used at 2 to 5 equivalents, and preferably, 2 and 3 equivalents with respect to the compound represented by Formula 4 for excellent economic feasibility. Here, as the used oxidant, meta-chloroperbenzoic acid (mCPBA), hydrogen peroxide or oxon may be used, and preferably, use of meta-chloroperbenzoic acid is the most effective.

In the second operation, in a reaction of substituting a sulfone with an $R^4$—H nucleophile, ethanol, methanol, dichloromethane ($CH_2Cl_2$), acetonitrile (MeCN), dichloroethane ($ClCH_2CH_2Cl$), dioxane, tetrahydrofuran (THF), N,N-dimethylformamide (DMF), N,N-dimethylacetamide (DMA), dimethylsulfoxide (DMSO) or acetone, and preferably, dichloromethane, is used as a solvent. As a base used in the reaction, N,N-diisopropylethylamine, triethylamine ($Et_3N$), methoxy sodium (NaOMe), or ethoxy sodium (NaOEt) may be representatively used, and the use of triethylamine is the most effective.

In addition, the progression of a reaction by a TLC method was confirmed during the reaction of producing the 2,5,6,7-tetrasubstituted thiazolo[4,5-b]pyridine derivative compound represented by Formula 1 according to the present invention, and a structure was analyzed and confirmed through NMR or a mass spectrum by isolating and purifying prepared derivative compounds represented by Formulas 1-1 to 1-110 (refer to Examples 1 and 2).

Hereinafter, exemplary examples are provided to help in understanding the present invention. However, the following examples are merely provided to more easily understand the present invention, but the scope of the present invention is not limited to the following examples.

Example 1. Synthesis of 2,5,6,7-tetrasubstituted thiazolo[4,5-b]pyridine derivative (Formula 1-1)

Operation 1: Synthesis of 2-(methylthio)-9-phenyl-5,6,7,8-tetrahydrothiazolo[4,5-b]quinoline

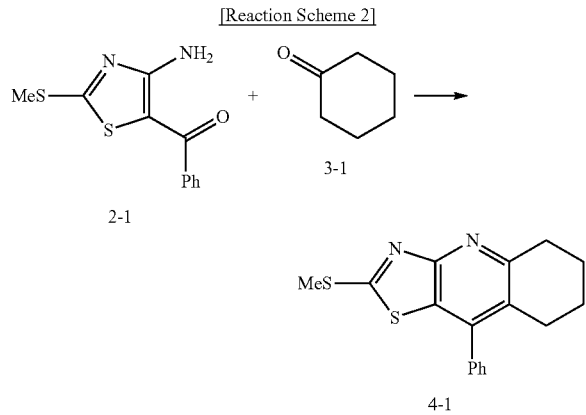

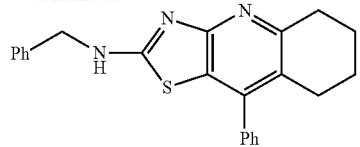

1-1

A 2-(methylthio)-9-phenyl-5,6,7,8-tetrahydrothiazolo[4,5-b]quinoline compound (500 mg, 1.60 mmol) represented by Formula 4-1 was dissolved in a dichloromethane (20 ml) solution and stirred at room temperature for 10 minutes, meta-chlorobenzoic acid (m-CPMA; 1.08 g, 4.80 mmol) was added at room temperature, and then stirred at room temperature for 12 hours during a reaction. After the reaction was completed by adding a 10% sodium thiosulfonate solution, extraction with water and ethylacetate was performed at room temperature, and a collected organic solution was dried and concentrated with anhydrous magnesium sulfate. The concentrated reaction mixture was dissolved in a dichloromethane solution (20 ml), and benzylamine (0.52 mL, 4.80 mmol) and triethylamine (0.67 mL, 4.80 mmol) were added at room temperature, and the resulting mixture was stirred and reacted at room temperature for 5 hours. After the reaction was completed, the reaction mixture obtained by concentration was isolated and purified through silica gel column chromatography under a mixed solvent of hexane/ethylacetate (3/12, v/v), thereby obtaining a yellow solid product represented by Formula 1-1, that is, an N-benzyl-9-phenyl-5,6,7,8-tetrahydrothiazolo[4,5-b]quinoline-2-amine compound (Example 1; 360 mg, yield: 61%) ($^1$H NMR (500 MHz, CDCl$_3$) δ 1.72 (m, 2H), 1.88 (m, 2H), 2.54 (t, J=6.3 Hz, 2H), 3.03 (t, J=6.5 Hz, 2H), 4.66 (s, 2H), 5.87 (br s, 1H), 7.27-7.38 (m, 7H), 7.39-7.48 (m, 3H); 13C NMR (125 MHz, CDCl3) δ 23.1, 23.2, 27.2, 33.1, 48.8, 123.0, 123.2, 127.7, 127.8, 128.0, 128.3, 128.7, 128.8, 137.5, 138.6, 142.9, 155.1, 161.5, 168.5; LC-MS (ESI) m/z 372 ([M+1]$^+$)).

Trichloroaluminum (800 mg, 6.0 mmol) was put into a solution prepared by dissolving [4-amino-2-(methylthio)thiazole-5-yl](phenyl)methanone (500 mg, 2.0 mmol) represented by Formula 2-1 and cyclohexanone (0.42 mL, 4.0 mmol) represented by Formula 3-1 in acetonitrile (MeCN; 30 mL), and stirred and heated during a reaction in an microwave oven at 150° C. for 15 minutes. After the reaction was completed, the resulting product was extracted with water and ethylacetate at room temperature, and the collected organic solution was dried and concentrated with anhydrous magnesium sulfate. The concentrated reaction mixture was isolated and purified through silica gel column chromatography using a mixed solvent of hexane/ethylacetate (5/1, v/v), thereby obtaining a yellow solid compound, for example, 2-(methylthio)-9-phenyl-5,6,7,8-tetrahydrothiazolo[4,5-b]quinoline compound (570 mg, yield: 91%) represented by Formula 4-1 ($^1$H NMR (500 MHz, CDCl$_3$) δ 1.75 (m, 2H), 1.92 (m, 2H), 2.62 (t, J=6.3 Hz, 2H), 2.80 (s, 3H), 3.11 (t, J=6.6 Hz, 2H), 7.31-7.33 (m, 2H), 7.42 (m, 1H), 7.46-7.48; $^{13}$C NMR (125 MHz, CDCl$_3$) δ 15.8, 22.9, 23.0, 27.4, 33.2, 125.8, 127.4, 127.9, 128.6, 128.9, 138.0, 143.3, 1256.5, 161.5, 171.8; LC-MS (ESI) m/z 313 ([M+1]$^+$)).

Operation 2: Synthesis of N-benzyl-9-phenyl-5,6,7,8-tetrahydrothiazolo[4,5-b]quinoline-2-amine

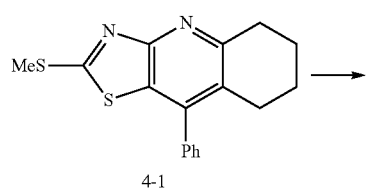

4-1

Example 2. Synthesis of 2,5,6,7-tetrasubstituted thiazolo[4,5-b]pyridine derivatives (Formulas 1-2 to 1-110)

2,5,6,7-tetrasubstituted thiazolo[4,5-b]pyridine derivatives were synthesized by the same method as described in Example 1, except that R$^1$, R$^2$, R$^3$ and R$^4$ in the compound represented by Formula 1 were changed as listed in Table 1. In addition, the analysis result for the synthesized 2,5,6,7-tetrasubstituted thiazolo[4,5-b]pyridine derivatives is shown in Table 1.

In addition, a degree of a reaction progress by a TLC method was confirmed during the production of the 2,5,6,7-tetrasubstituted thiazolo[4,5-b]pyridine derivative compound represented by Formula 1 according to the present invention, and the produced compound represented by Formula 1 was isolated and purified to analyze and confirm a structure through NMR or a mass spectrum. The result is shown in Table 1.

TABLE 1

[화학식1]

| 화합물 | R¹ | R² | R³ | R⁴ | 분석자료[¹H NMR (500 MHz, CDCl₃) δ LC/MS (ESI)] |
|---|---|---|---|---|---|
| 1-1 | Ph | —(CH₂)₃— | | BnNH— | ¹H NMR (500 MHz, CDCl₃) δ 1.69-1.74 (m, 2H), 1.85-1.90 (m, 2H), 2.54 (t, J = 6.3 Hz, 2H), 3.03 (t, J = 6.5 Hz, 2H), 4.66 (s, 2H), 5.87 (br s, 1H), 7.27-7.38 (m, 7H), 7.39-7.48 (m, 3H): LC-MS (ESI) m/z 372 ([M + 1]⁺). |
| 1-2 | Ph | —(CH₂)₃— | | 4-MeO—BnNH— | ¹H NMR (500 MHz, CDCl₃) δ 1.69-1.75 (m, 2H), 1.85-1.91 (m, 2H), 2.54 (t, J = 6.3 Hz, 2H), 3.03 (t, J = 6.6 Hz, 2H), 3.78 (s, 3H), 4.58 (s, 2H), 5.71 (br s, 1H), 6.85 (d, J = 8.7 Hz, 2H), 7.29 (d, J = 8.7 Hz, 2H), 7.30-7.34 (m, 2H), 7.41 (m, 1H), 7.44-7.48 (m, 2H): LC-MS (ESI) m/z 402 ([M + 1]⁺). |
| 1-3 | Ph | —(CH₂)₃— | | 2-MeO—BnNH— | LC-MS (ESI) m/z 402 ([M + 1]⁺). |
| 1-4 | Ph | —(CH₂)₃— | | 4-Me—BnNH— | LC-MS (ESI) m/z 386 ([M + 1]⁺). |
| 1-5 | Ph | —(CH₂)₃— | | 3-F—BnNH— | LC-MS (ESI) m/z 390 ([M + 1]⁺). |
| 1-6 | Ph | —(CH₂)₃— | | 3-Cl—BnNH— | LC-MS (ESI) m/z 406 ([M + 1]⁺). |
| 1-7 | Ph | —(CH₂)₃— | | morpholin-4-yl | ¹H NMR (500 MHz, CDCl₃) δ 1.71-1.75 (m, 2H), 1.87-1.91 (m, 2H), 2.56 (t, J = 6.3 Hz, 2H), 3.04 (t, J = 6.6 Hz, 2H), 3.63 (t, J = 4.8 Hz, 4H), 3.76 (t, J = 3.8 Hz, 4H), 7.31-7.35 (m, 2H), 7.40-7.50 (m, 3H): LC-MS (ESI) m/z 352 ([M + 1]⁺). |
| 1-8 | Ph | —(CH₂)₃— | | piperidin-1-yl | ¹H NMR (500 MHz, CDCl₃) δ 1.61-1.68 (m, 6H), 1.69-1.74 (m, 2H), 1.85-1.89 (m, 2H), 2.53 (t, J = 6.3 Hz, 2H), 3.01 (t, J = 6.6 Hz, 2H), 3.55-3.62 (m, 4H), 7.31-7.34 (m, 2H), 7.40 (m, 1H), 7.44-7.48 (m, 3H): LC-MS (ESI) m/z 350 ([M + 1]⁺). |
| 1-9 | Ph | —(CH₂)₃— | | Et₃N— | LC-MS (ESI) m/z 338 ([M + 1]⁺). |
| 1-10 | Ph | —(CH₂)₃— | | BnMeN— | LC-MS (ESI) m/z 386 ([M + 1]⁺). |
| 1-11 | Ph | —(CH₂)₃— | | n-PrNH— | ¹H NMR (500 MHz, CDCl₃) δ 0.96 (t, J = 7.4 Hz, 3H), 1.53-1.55 (m, 4H), 1.57-1.58 (m, 2H), 2.54 (t, J = 6.3 Hz, 2H), 3.02 (t, J = 6.6 Hz, 2H), 3.38 (t, J = 7.2 Hz, 2H), 5.73 (br s, 1H), 7.31-7.34 (m, 2H), 7.41 (m, 1H), 7.45-7.49 (m, 2H): LC-MS (ESI) m/z 324 ([M + 1]⁺). |
| 1-12 | Ph | —(CH₂)₃— | | pyrrolidin-1-yl | ¹H NMR (500 MHz, CDCl₃) δ 1.69-1.77 (m, 4H), 1.85-1.91 (m, 2H), 2.02-2.06 (m, 4H), 2.54 (t, J = 6.3 Hz, 2H), 3.02 (t, J = 6.6 Hz, 2H), 3.43-3.59 (m, 4H), 7.32-7.35 (m, 2H), 7.41 (m, 1H), 7.45-7.49 (m, 2H): LC-MS (ESI) m/z 336 ([M + 1]⁺). |
| 1-13 | Ph | —(CH₂)₃— | | cyclohexylmethyl-NH— | ¹H NMR (500 MHz, CDCl₃) δ 0.93-1.99 (m, 2H), 1.09-1.29 (m, 3H), 1.64-1.78 (m, 8H), 1.84-1.90 (m, 2H), 2.53 (t, J = 6.3 Hz, 2H), 3.02 (t, J = 6.6 Hz, 2H), 3.24 (d, J = 6.8 Hz, 2H), 5.26 (br s, 1H), 7.31-7.34 (m, 2H), 7.41 (m, 1H), 7.44-7.49 (m, 2H): LC-MS (ESI) m/z 378 ([M + 1]⁺). |
| 1-14 | Ph | —CH₂SHCH₂— | | BnNH— | LC-MS (ESI) m/z 390 ([M + 1]⁺). |
| 1-15 | Ph | —CH₂SHCH₂— | | 4-MeO—BnNH— | LC-MS (ESI) m/z 420 ([M + 1]⁺). |
| 1-16 | Ph | —CH₂SHCH₂— | | morpholin-4-yl | LC-MS (ESI) m/z 370 ([M + 1]⁺). |
| 1-17 | Ph | —CH₂SHCH₂— | | n-PrNH— | LC-MS (ESI) m/z 342 ([M + 1]⁺). |
| 1-18 | Ph | —CH₂SHCH₂— | | pyrrolidin-1-yl | LC-MS (ESI) m/z 354 ([M + 1]⁺). |
| 1-19 | Ph | —(CH₂)₂— | | BnNH— | ¹H NMR (500 MHz, CDCl₃) δ 2.08-2.17 (m, 2H), 2.93 (t, J = 7.2, Hz, 2H), 3.10 (t, J = 7.6 Hz, 2H), 4.67 (s, 2H), 5.69 (br s, 1H), 7.28-7.44 (m, 6H), 7.46-7.52 (m, 4H): LC-MS (ESI) m/z 358 ([M + 1]⁺). |

TABLE 1-continued

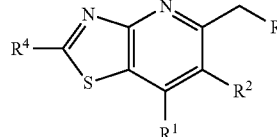

| 화합물 | R¹ | R² | R³ | R⁴ | 분석자료[¹H NMR (500 MHz, CDCl₃) δ LC/MS (ESI)] |
|---|---|---|---|---|---|
| 1-20 | Ph | —(CH₂)₂— | | 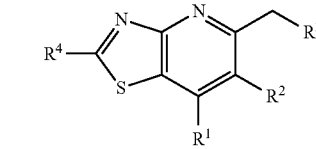 | ¹H NMR (500 MHz, CDCl₃) δ 2.08-2.17 (m, 2H), 2.94 (t, J = 7.3, Hz, 2H), 3.10 (t, J = 7.6 Hz, 2H), 3.63-3.68 (m, 4H), 3.78-7.83 (m, 4H), 7.41-7.46 (m, 1H), 7.47-7.54 (m, 4H):LC-MS (ESI) m/z 338 ([M + 1]⁺). |
| 1-21 | Ph | —(CH₂)₂— | | 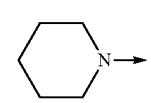 | ¹H NMR (500 MHz, CDCl₃) δ 1.64-1.70 (m, 6H), 2.11 (m, 2H), 2.92 (t, J = 7.3 Hz, 2H), 3.08 (t, J = 7.6 Hz, 2H), 3.58-3.65 (m, 4H), 7.38-7.43 (m, 1H), 7.44-7.54 (m, 4H): LC-MS (ESI) m/z 336 ([M + 1]⁺). |
| 1-22 | Ph | —(CH₂)₂— | | n-PrNH— | ¹H NMR (500 MHz, CDCl₃) δ 0.98 (t, J = 7.4 Hz, 3H), 1.66-1.73 (m, 2H), 2.12 (tt, J = 7.4, 7.4 Hz, 2H), 3.09 (t, J = 7.6 Hz, 2H), 3.39 (t, J = 7.0 Hz, 2H), 5.52 (br s, 1H), 7.40-7.44 (m, 1H), 7.46-7.52 (m, 4H): LC-MS (ESI) m/z 310 ([M + 1]⁺). |
| 1-23 | Ph | —(CH₂)₂— | | 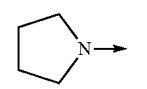 | ¹H NMR (500 MHz, CDCl₃) δ 2.04-2.07 (m, 4H), 2.11 (m, 2H), 2.92 (t, J = 7.3 Hz, 2H), 3.08 (t, J = 7.6 Hz, 2H), 3.51-3.63 (m, 4H), 7.40-7.44 (m, 1H), 7.46-7.55 (m, 4H): LC-MS (ESI) m/z 322 ([M + 1]⁺). |
| 1-24 | Ph | —(CH₂)₂— | |  | ¹H NMR (500 MHz, CDCl₃) δ 0.94-1.02 (m, 2H), 1.11-1.29 (m, 3H), 1.63-1.76 (m, 4H), 1.76-1.82 (m, 2H), 2.12 (m, 2H), 2.92 (t, J = 7.3 Hz, 2H), 3.09 (t, J = 7.3 Hz, 2H), 3.25 (d, J = 8.6 Hz, 2H), 5.48 (br s, 1H), 7.40-7.44 (m, 1H), 7.46-7.52 (m, 4H): LC-MS (ESI) m/z 364 ([M + 1]⁺). |
| 1-25 | Ph | —(CH₂)₂— | | 4-MeO—BnNH— | ¹H NMR (500 MHz, CDCl₃) δ 2.12 (m, 2H), 2.92 (t, J = 7.3 Hz, 2H), 3.09 (t, J = 7.6 Hz, 2H), 3.79 (s, 3H), 4.58 (s, 2H), 5.87 (br s, 1H), 6.86 (d, J = 6.6 Hz, 2H), 7.30 (d, J = 8.6 Hz, 2H), 7.39-7.43 (m, 1H), 7.45-7.50 (m, 4H): LC-MS (ESI) m/z 388 ([M + 1]⁺). |
| 1-26 | Ph | —CH₂OCH₂— | | BnNH— | LC-MS (ESI) m/z 373 ([M + 1]⁺). |
| 1-27 | Ph | —CH₂OCH₂— | | 4-MeO—BnNH— | LC-MS (ESI) m/z 403 ([M + 1]⁺). |
| 1-28 | Ph | —CH₂OCH₂— | | 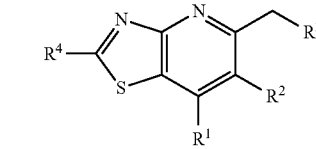 | LC-MS (ESI) m/z 353 ([M + 1]⁺). |
| 1-29 | Ph | —CH₂OCH₂— | | 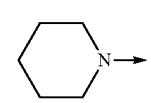 | LC-MS (ESI) m/z 351 ([M + 1]⁺). |
| 1-30 | Ph | —CH₂OCH₂— | | n-PrNH— | LC-MS (ESI) m/z 325 ([M + 1]⁺). |
| 1-31 | Ph | —CH₂OCH₂— | | 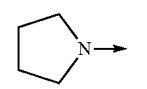 | LC-MS (ESI) m/z 337 ([M + 1]⁺). |
| 1-32 | Ph | —(CH₂)₄— | | BnNH— | ¹H NMR (500 MHz, CDCl₃) δ 1.35-1.62 (m, 2H), 1.73-1.79 (m, 2H), 1.83-1.89 (m, 2H), 2.65-2.69 (m, 2H), 3.14-3.18 (m, 2H), 4.67 (s, 2H), 5.54 (br s, 1H), 7.26-7.38 (m, 7H), 7.41 (m, 1H), 7.44-7.48 (m, 2H): LC-MS (ESI) m/z 386 ([M + 1]⁺). |
| 1-33 | Ph | —(CH₂)₄— | | 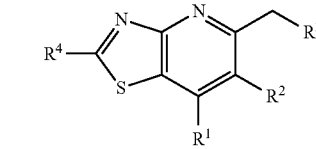 | ¹H NMR (500 MHz, CDCl₃) δ 1.56-1.62 (m, 2H), 1.74-1.79 (m, 2H), 1.83-1.88 (m, 2H), 2.66-2.70 (m, 2H), 3.14-3.18 (m, 2H), 3.61-3.64 (m, 4H), 3.76-3.79 (m, 4H), 7.30-7.33 (m, 2H), 7.43 (m, 1H), 7.46-7.50 (m, 2H): LC-MS (ESI) m/z 366 ([M + 1]⁺). |
| 1-34 | Ph | —(CH₂)₄— | | 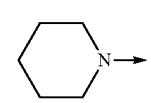 | ¹H NMR (500 MHz, CDCl₃) δ 1.55-1.60 (m, 2H), 1.60-1.68 (m, 6H), 1.73-1.79 (m, 2H), 1.83-1.88 (m, 2H), 2.64-2.68 (m, 2H), 3.12-3.16 (m, 2H), 3.57-3.61 (m, 4H), 7.30-7.33 (m, 2H), 7.41 (m, 1H), 7.45-7.50 (m, 2H): LC-MS (ESI) m/z 364 ([M + 1]⁺). |

TABLE 1-continued

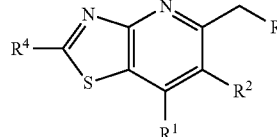

| | R¹ | R² | R³ | R⁴ | [¹H NMR (500 MHz, CDCl₃) δ LC/MS (ESI)] |
|---|---|---|---|---|---|
| 1-35 | Ph | —(CH₂)₄— | | 4-MeO—BnNH— | ¹H NMR (500 MHz, CDCl₃) δ 1.56-1.62 (m, 2H), 1.74-1.79 (m, 2H), 1.83-1.88 (m, 2H), 2.65-2.69 (m, 2H), 3.13-3.18 (m, 2H), 3.79 (s, 3H), 4.59 (s, 2H), 5.48 (br s, 1H), 6.86 (d, J = 8.6 Hz, 2H), 7.28-7.32 (m, 4H), 7.39-7.49 (m, 3H): LC-MS (ESI) m/z 416 ([M + 1]⁺). |
| 1-36 | Ph | —(CH₂)₄— | | n-PrNH— | ¹H NMR (500 MHz, CDCl₃) δ 0.96 (t, J = 7.4 Hz, 3H), 1.58 (m, 2H), 1.69 (q, J = 7.3 Hz, 2H), 1.73-1.77 (m, 2H), 1.82-1.87 (m, 2H), 2.64-2.67 (m, 2H), 3.13-3.15 (m, 2H), 3.33 (t, J = 6.7 Hz, 2H), 5.39 (br s, 1H), 7.30-7.32 (m, 2H), 7.40-7.50 (m, 3H): LC-MS (ESI) m/z 338 ([M + 1]⁺). |
| 1-37 | Ph | —(CH₂)₄— | | n-BuNH— | ¹H NMR (500 MHz, CDCl₃) δ 7.49-7.44 (m, 2H), 7.42 (m, 1H), 7.33-7.39 (m, 2H), 5.58 (br s, 1H), 3.41 (t, J = 7.1 Hz, 2H), 3.19-3.11 (m, 2H), 2.71-2.62 (m, 2H), 1.88-1.81 (m, 2H), 1.80-1.72 (m, 2H), 1.70-1.62 (m, 2H), 1.62-1.54 (m, 2H), 1.44-1.35 (m, 2H), 0.93 (t, J = 7.4 Hz, 3H): LC-MS (ESI) m/z 352 ([M + 1]⁺). |
| 1-38 | Ph | —(CH₂)₄— | | 2,4-di-MeO—BnNH— | ¹H NMR (500 MHz, CDCl₃) δ 7.49-7.38 (m, 3H), 7.32-7.27 (m, 2H), 6.44 (d, J = 2.3 Hz, 1H), 6.41 (dd, J = 2.3, 8.2 Hz, 1H), 5.64 (br s, 1H), 4.56 (d, J = 2.7 Hz, 2H), 3.81 (s, 3H), 3.78 (s, 3H), 3.18-3.12 (m, 2H), 2.69-2.62 (m, 2H), 1.89-1.81 (m, 2H), 1.80-1.72 (m, 2H), 1.60-1.52 (m, 2H): LC-MS (ESI) m/z 446 ([M + 1]⁺). |
| 1-39 | Ph | —(CH₂)₄— | | 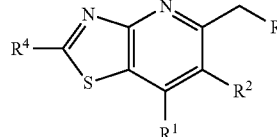 | ¹H NMR (500 MHz, CDCl₃) δ 1.55-1.61 (m, 2H), 1.73-1.77 (m, 2H), 1.81-1.87 (m, 2H), 2.01-2.05 (m, 4H), 2.64-2.67 (m, 2H), 3.13-3.15 (m, 2H), 3.46-3.58 (m, 4H), 7.31-7.34 (m, 2H), 7.42 (m, 1H), 7.45-7.50 (m, 2H): LC-MS (ESI) m/z 350 ([M + 1]⁺). |
| 1-40 | Ph | —(CH₂)₄— | | 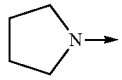 | ¹H NMR (500 MHz, CDCl₃) δ 0.94 (dq, J = 3.0, 12.1 Hz, 2H), 1.11-1.27 (m, 3H), 1.51-1.5.9 (m, 2H), 1.62-1.79 (m, 8H), 1.82-1.87 (m, 2H), 2.64-2.67 (m, 2H), 3.12-3.15 (m, 2H), 3.24 (d, J = 6.5 Hz, 2H), 5.51 (br s, 1H), 7.29-7.32 (m, 2H), 7.42 (m, 1H), 7.45-7.49 (m, 2H): LC-MS (ESI) m/z 392 ([M + 1]⁺). |
| 1-41 | Ph | —CH₂NHCH₂— | | BnNH— | LC-MS (ESI) m/z 373 ([M + 1]⁺). |
| 1-42 | Ph | —CH₂NHCH₂— | | 4-MeO—BnNH— | LC-MS (ESI) m/z 403 ([M + 1]⁺). |
| 1-43 | Ph | —CH₂NHCH₂— | | 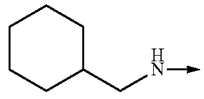 | LC-MS (ESI) m/z 353 ([M + 1]⁺). |
| 1-44 | Ph | —CH₂NHCH₂— | | n-PrNH— | LC-MS (ESI) m/z 325 ([M + 1]⁺). |
| 1-45 | Ph | —CH₂NHCH₂— | | 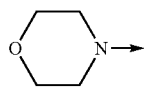 | LC-MS (ESI) m/z 337 ([M + 1]⁺). |
| 1-46 | Ph | —CO(CH₂)₂— | | BnNH— | ¹H NMR (500 MHz, CDCl₃) δ 2.17 (m, 2H), 2.61 (d, J = 6.6 Hz, 2H), 3.24 (d, J = 6.2 Hz, 2H), 4.70 (s, 2H), 6.03 (br s, 1H), 7.24-7.26 (m, 2H), 7.32 (m, 1H), 7.34-7.37 (m, 4H), 7.39-7.45 (m, 2H): LC-MS (ESI) m/z 386 ([M + 1]⁺). |
| 1-47 | Ph | —CO(CH₂)₂— | | 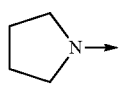 | ¹H NMR (500 MHz, CDCl₃) δ 2.17 (tt, J = 6.4, 6.4 Hz, 2H), 2.16 (t, J = 6.6 Hz, 2H), 3.23 (t, J = 6.3 Hz, 4H), 3.77-3.75 (m,4H), 3.77-3.81 (m, 4H), 7.24-7.27 (m, 2H), 7.40-7.48 (m, 3H): LC-MS (ESI) m/z 366 ([M + 1]⁺). |
| 1-48 | Ph | —CO(CH₂)₂— | | 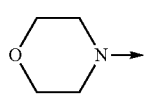 | ¹H NMR (500 MHz, CDCl₃) δ 1.66-1.73 (m, 6H), 2.16 (m, 2H), 2.60 (t, J = 6.6 Hz, 2H), 3.21 (t, J = 6.3 Hz, 2H), 3.57-3.79 (m, 4H), 7.24-7.27 (m, 2H), 7.39-7.47 (m, 3H): LC-MS (ESI) m/z 364 ([M + 1]⁺). |
| 1-49 | Ph | —CO(CH₂)₂— | | 4-MeO—BnNH— | ¹H NMR (500 MHz, CDCl₃) δ 2.14-2.19 (m, 2H), 2.60 (t, J = 6.6 Hz, 2H), 3.21 (t, J = 6.2 Hz, 2H), 3.78 (s, 3H), 4.59 (s, 2H), 6.04 (br s, 1H), 6.85 (d, J = 8.8 Hz, 2H), 7.22-7.25 (m, |

TABLE 1-continued

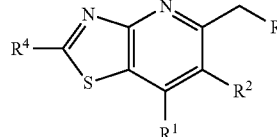

| 화합물 | R¹ | R² | R³ | R⁴ | 분석자료[¹H NMR (500 MHz, CDCl₃) δ LC/MS (ESI)] |
|---|---|---|---|---|---|
| | | | | | 2H), 7.27 (d, J = 8.7 Hz, 2H), 7.40-7.48 (m, 3H): LC-MS (ESI) m/z 416 ([M + 1]⁺). |
| 1-50 | Ph | —CO(CH₂)₂— | | n-PrNH— | ¹H NMR (500 MHz, CDCl₃) δ 0.98 (t, J = 7.4 Hz, 3H), 1.72 (q, J = 7.3 Hz, 2H), 2.16 (m, 2H), 2.60 (t, J = 6.6 Hz, 2H), 3.23 (t, J = 6.3 Hz, 2H), 3.38-3.47 (m, 2H), 5.93 (br s, 1H), 7.24-7.26 (m, 2H), 7.40-7.47 (m, 3H): LC-MS (ESI) m/z 338 ([M + 1]⁺). |
| 1-51 | Ph | —CO(CH₂)₂— | | 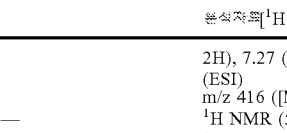 | ¹H NMR (500 MHz, CDCl₃) δ 2.06-2.09 (m, 4H), 2.16 (m, 2H), 2.60 (t, J = 6.6 Hz, 2H), 3.22 (t, J = 6.3 Hz, 2H), 3.28-3.39 (m, 2H), 3.76-3.92 (m, 2H), 7.25-7.28 (m, 2H), 7.38-7.47 (m, 3H): LC-MS (ESI) m/z 350 ([M + 1]⁺). |
| 1-52 | Ph | —CO(CH₂)₂— | | 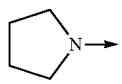 | ¹H NMR (500 MHz, CDCl₃) δ 0.95-1.00 (m, 2H), 1.13-1.31 (m, 3H), 1.66-1.79 (m, 6H), 2.13-2.19 (m, 2H), 3.60 (t, J = 6.6 Hz, 2H), 3.22 (t, J = 6.3 Hz, 2H), 3.28 (s, 2H), 7.24-7.26 (m, 2H), 7.40-7.47 (m, 3H): LC-MS (ESI) m/z 392 ([M + 1]⁺). |
| 1-53 | Ph | Me | Me | BnNH— | ¹H NMR (500 MHz, CDCl₃) δ 1.36 (t, J = 7.5 Hz, 3H), 2.16 (s, 3H), 2.92 (q, J = 7.5 Hz, 2H), 4.69 (s, 2H), 5.51 (br s, 1H), 7.27-7.37 (m, 7H), 7.40-7.44 (m, 1H), 7.45-7.49 (m, 2H): LC-MS (ESI) m/z 360 ([M + 1]⁺). |
| 1-54 | Ph | Me | Me | 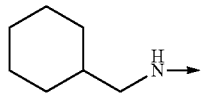 | ¹H NMR (500 MHz, CDCl₃) δ 1.36 (t, J = 7.5 Hz, 3H), 2.17 (s, 3H), 2.91 (q, J = 7.5 Hz, 2H), 3.62-3.66 (m, 4H), 3.77-3.80 (m, 4H), 7.33-7.36 (m, 2H), 7.43 (m, 1H), 7.47-7.51 (m, 2H): LC-MS (ESI) m/z 340 ([M + 1]⁺). |
| 1-55 | Ph | Me | Me | 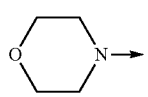 | ¹H NMR (500 MHz, CDCl₃) δ 1.35 (t, J = 7.6 Hz, 3H), 1.62-1.63 (m, 6H), 2.15 (s, 3H), 2.89 (q, J = 7.5 Hz, 2H), 3.58-3.63 (m, 4H), 7.32-7.35 (m, 2H), 7.42 (m, 1H), 7.45-7.50 (m, 2H): LC-MS (ESI) m/z 338 ([M + 1]⁺). |
| 1-56 | Ph | Me | Me | 4-MeO—BnNH— | ¹H NMR (500 MHz, CDCl₃) δ 1.36 (t, J = 7.5 Hz, 3H), 2.16 (s, 3H), 2.91 (q, J = 7.5 Hz, 2H), 3.79 (s, 3H), 4.61 (s, 2H), 5.46 (br s, 1H), 6.87 (d, J = 8.7 Hz, H), 7.29 (d, J = 8.8 Hz, 2H), 7.31-7.34 (m, 2H), 7.41 (m, 1H), 7.45-7.49 (m, 2H): LC-MS (ESI) m/z 390 ([M + 1]⁺). |
| 1-57 | Ph | Me | Me | n-PrNH— | ¹H NMR (500 MHz, CDCl₃) δ 0.97 (t, J = 7.4 Hz, 3H), 1.35 (q, J = 7.5 Hz, 2H), 1.69 (q, J = 7.3 Hz, 2H), 2.90 (q, J = 7.5 Hz, 2H), 3.37-3.43 (m, 2H), 5.37 (br s, 1H), 7.32-7.35 (m, 2H), 7.42 (m, 1H), 7.46-7.50 (m, 2H): LC-MS (ESI) m/z 312 ([M + 1]⁺). |
| 1-58 | Ph | Me | Me | 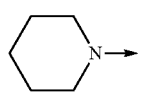 | ¹H NMR (500 MHz, CDCl₃) δ 1.36 (t, J = 7.5 Hz, 3H), 2.02-2.04 (m, 4H), 2.15 (s, 3H), 2.90 (q, J = 7.5 Hz, 2H), 3.46-3.63 (m, 4H), 7.33-7.36 (m, 2H), 7.42 (m, 1H), 7.46-7.50 (m, 2H): LC-MS (ESI) m/z 324 ([M + 1]⁺). |
| 1-59 | Ph | Me | Me | 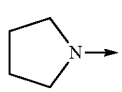 | ¹H NMR (500 MHz, CDCl₃) δ 0.95 (dq, J = 3.0, 12.0 Hz, 2H), 1.12-1.27 (m, 3H), 1.35 (t, J = 7.5 Hz, 2H), 1.61-1.79 (m, 8H), 2.15 (s, 3H), 2.90 (q, J = 7.5 Hz, 2H), 3.26 (d, J = 5.4 Hz, 2H), 5.51 (br s, 1H), 7.32-7.34 (m, 2H), 7.42 (m, 1H), 7.46-7.49 (m, 1H): LC-MS (ESI) m/z 356 ([M + 1]⁺). |
| 1-60 | Ph | H | H | BnNH— | LC-MS (ESI) m/z 332 ([M + 1]⁺). |
| 1-61 | Ph | H | H | 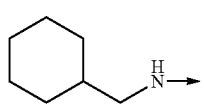 | LC-MS (ESI) m/z 310 ([M + 1]⁺). |
| 1-62 | 4-MeO—Ph | —(CH₂)₃— | | BnNH— | ¹H NMR (500 MHz, CDCl₃) δ 1.70-1.75 (m, 2H), 1.87-1.92 (m, 2H), 2.56 (t, J = 6.3 Hz, 2H), 3.03 (t, J = 6.6 Hz, 2H), 3.86 (s, 2H), 5.63 (br s, 1H), 6.98 (d, J = 3.8 Hz, 2H), 7.26 (d, J = 8.8 Hz, 2H), 7.27-7.39 (m, 5H): LC-MS (ESI) m/z 401 ([M + 1]⁺). |

US 9,932,355 B2

TABLE 1-continued

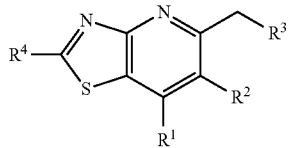

| No. | R¹ | R² | R³ | R⁴ | ¹H NMR (500 MHz, CDCl₃) δ LC/MS (ESI) |
|---|---|---|---|---|---|
| 1-63 | 4-MeO—Ph | | —(CH₂)₃— | morpholin-N-yl | ¹H NMR (500 MHz, CDCl₃) δ 1.71-1.76 (m, 2H), 1.86-1.91 (m, 2H), 2.57 (t, J = 6.3 Hz, 2H), 3.02 (t, J = 6.6 Hz, 2H), 3.61-3.64 (m, 4H), 3.76-7.79 (m, 4H), 3.86 (s, 3H), 6.99 (d, J = 8.8 Hz, 2H), 7.27 (d, J = 8.8 Hz, 2H): LC-MS (ESI) m/z 382 ([M + 1]⁺). |
| 1-64 | 4-MeO—Ph | | —(CH₂)₃— | piperidin-N-yl | ¹H NMR (500 MHz, CDCl₃) δ 1.63-1.68 (m, 6H), 1.70-1.75 (m, 2H), 1.85-1.90 (m, 2H), 2.55 (t, J = 6.3 Hz, 3H), 3.01 (t, J = 6.6 Hz, 2H), 3.58-3.63 (m, 4H), 3.86 (s, 3H), 6.99 (d, J = 8.8 Hz, 2H), 7.28 (d, J = 8.8 Hz, 2H): LC-MS (ESI) m/z 380 ([M + 1]⁺). |
| 1-65 | 4-MeO—Ph | | —(CH₂)₃— | 4-MeO—BnNH— | ¹H NMR (500 MHz, CDCl₃) δ 1.70-1.77 (m, 2H), 1.86-1.92 (m, 2H), 2.56 (t, J = 6.3 Hz, 3H), 3.03 (t, J = 6.6 Hz, 2H), 3.79 (s, 3H), 3.86 (s, 3H), 4.59 (s, 2H), 5.58 (br s, 1H), 6.86 (d, J = 8.7 Hz, 2H), 6.98 (d, J = 8.7 Hz, 2H), 7.26 (d, J = 8.7 Hz, 2H), 7.29 (d, J = 8.7 Hz, 2H): LC-MS (ESI) m/z 432 ([M + 1]⁺). |
| 1-66 | 4-MeO—Ph | | —(CH₂)₃— | n-PrNH— | ¹H NMR (500 MHz, CDCl₃) δ 0.97 (t, J = 7.4 Hz, 3H), 1.69 (q, J = 7.3 Hz, 2H), 1.71-1.45 (m, 2H), 1.85-1.91 (m, 2H), 2.56 (t, J = 6.3 Hz, 2H), 3.02 (t, J = 6.5 Hz, 2H), 3.39 (t, J = 6.8 Hz, 2H), 5.38 (br s, 1H), 6.99 (d, J = 8.7 Hz, 2H), 7.27 (d, J = 8.7 Hz, 2H): LC-MS (ESI) m/z 354 ([M + 1]⁺). |
| 1-67 | 4-MeO—Ph | | —(CH₂)₃— | n-BuNH— | ¹H NMR (500 MHz, CDCl₃) δ 7.27 (d, J = 8.5 Hz, 2H), 6.99 (d, J = 8.5 Hz, 2H), 5.72 (br s, 1H), 3.87 (s, 3H), 3.42 (t, J = 6.9 Hz, 2H), 3.01 (t, J = 6.3 Hz, 2H), 2.55 (t, J = 6.2 Hz, 2H), 1.93-1.83 (m, 2H), 1.75-1.69 (m, 2H), 1.69-1.62 (m, 2H), 1.44-1.35 (m, 2H), 0.93 (t, J = 7.4 Hz, 3H): LC-MS (ESI) m/z 368 ([M + 1]⁺). |
| 1-68 | 4-MeO—Ph | | —(CH₂)₃— | pyrrolidin-N-yl | ¹H NMR (500 MHz, CDCl₃) δ 1.70-1.75 (m, 2H), 1.85-1.90 (m, 2H), 2.02-2.05 (m, 4H), 2.56 (d, J = 6.3 Hz, 2H), 3.02 (t, J = 6.6 Hz, 2H), 3.40-3.63 (m, 4H), 3.87 (s, 3H), 7.00 (d, J = 8.7 Hz, 2H), 7.29 (d, J = 8.7 Hz, 2H): LC-MS (ESI) m/z 366 ([M + 1]⁺). |
| 1-69 | 4-MeO—Ph | | —(CH₂)₃— | cyclohexylmethyl-NH— | ¹H NMR (500 MHz, CDCl₃) δ 0.97 (m, 2H), 1.21 (m, 3H), 1.64-1.78 (m, 8H), 1.85-1.90 (m, 2H), 2.55 (t, J = 6.2 Hz, 2H), 3.02 (t, J = 6.6 Hz, 2H), 3.26 (d, J = 5.1 Hz, 2H), 3.87 (s, 3H), 5.42 (br s, 1H), 6.99 (d, J = 8.7 Hz, 2H), 7.27 (d, J = 8.7 Hz, 2H): LC-MS (ESI) m/z 366 ([M + 1]⁺). |
| 1-70 | 4-MeO—Ph | | —(CH₂)₃— | 2,4-di-MeO—BnNH— | ¹H NMR (500 MHz, DMSO-d₆) δ 8.43 (t, J = 4.7 Hz, 1H), 7.30 (d, J = 8.7 Hz, 2H), 7.19 (d, J = 8.3 Hz, 1H), 7.05 (d, J = 8.7 Hz, 2H), 6.57 (d, J = 2.3 Hz, 1H), 6.48 (dd, J = 8.3, 2.4 Hz, 1H), 4.44 (d, J = 5.2 Hz, 2H), 3.81 (s, 3H), 3.80 (s, 3H), 1.74 (s, 3H), 2.83 (t, J = 6.5 Hz, 2H), 2.47 (t, J = 6.5 Hz, 4H), 1.83-1.77 (m, 2H), 1.73-1.56 (m, 2H): LC-MS (ESI) m/z ([M + 1]⁺). |
| 1-71 | 4-MeO—Ph | | —(CH₂)₄— | BnNH— | ¹H NMR (500 MHz, CDCl₃) δ 1.55-1.62 (m, 4H), 1.75-1.80 (m, 2H), 1.82-1.88 (m, 2H), 2.67-2.72 (m, 2H), 3.13-3.18 (m, 2H), 3.87 (s, 3H), 4.67 (s, 2H), 5.50 (br s, 1H), 6.99 (d, J = 8.7 Hz, 2H), 7.24 (d, J = 8.7 Hz, 2H), 7.27-7.39 (m, 5H): LC-MS (ESI) m/z 416 ([M + 1]⁺). |
| 1-72 | 4-MeO—Ph | | —(CH₂)₄— | morpholin-N-yl | ¹H NMR (500 MHz, CDCl₃) δ 1.58-1.62 (m, 2H), 1.74-1.79 (m, 2H), 1.83-1.88 (m, 2H), 2.68-2.72 (m, 2H), 3.13-3.18 (m, 2H), 3.61-3.64 (m, 4H), 3.76-3.79 (m, 4H), 3.87 (s, 3H), 7.00 (d, J = 8.8 Hz, 2H), 7.25 (d, J = 8.8 Hz, 2H): LC-MS (ESI) m/z 396 ([M + 1]⁺). |
| 1-73 | 4-MeO—Ph | | —(CH₂)₄— | piperidin-N-yl | ¹H NMR (500 MHz, CDCl₃) δ 1.56-1.61 (m, 4H), 1.61-1.68 (m, 6H), 1.72-1.78 (m, 2H), 1.82-1.88 (m, 2H), 2.66-2.69 (m, 2H), 3.11-3.15 (m, 2H), 3.58-3.62 (m, 4H), 3.87 (s, 3H), 6.99 (d, J = 8.8 Hz, 2H), 7.25 (d, J = 8.8 Hz, 2H): LC-MS (ESI) m/z 394 ([M + 1]⁺). |
| 1-74 | 4-MeO—Ph | | —(CH₂)₄— | 4-MeO—BnNH— | ¹H NMR (500 MHz, CDCl₃) δ 1.57-1.63 (m, 2H), 1.73-1.80 (m, 2H), 1.84-1.89 (m, 2H), 3.78 (s, 3H), 3.87 (s, 3H), 4.59 |

TABLE 1-continued

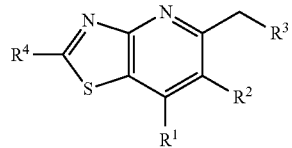

| | R¹ | R² | R³ | R⁴ | [¹H NMR (500 MHz, CDCl₃) δ LC/MS (ESI)] |
|---|---|---|---|---|---|
| | | | | | (s, 2H), 5.47 (br s, 1H), 6.89 (d, J = 8.7 Hz, 2H), 6.99 (d, J = 8.7 Hz, 2H), 7.24 (d, J = 8.7 Hz, 2H), 7.29 (d, J = 8.7 Hz, 2H): LC-MS (ESI) m/z 446 ([M + 1]⁺). |
| 1-75 | 4-MeO—Ph | —(CH₂)₄— | | n-PrNH— | ¹H NMR (500 MHz, CDCl₃) δ 0.96 (t, J = 7.4 Hz, 3H), 1.58 (m, 2H), 1.69 (q, J = 7.3 Hz, 2H), 1.73-1.78 (m, 2H), 1.82-1.87 (m, 2H), 2.66-2.69 (m, 2H), 3.12-3.14 (m, 2H), 3.38 (t, J = 7.1 Hz, 2H), 3.87 (s, 3H), 5.54 (br s, 1H), 6.99 (d, J = 8.7 Hz, 2H), 7.24 (d, J = 8.7 Hz, 2H): LC-MS (ESI) m/z 368 ([M + 1]⁺). |
| 1-76 | 4-MeO—Ph | —(CH₂)₄— | | pyrrolidin-1-yl | ¹H NMR (500 MHz, CDCl₃) δ 1.57-1.60 (m, 2H), 1.74-1.77 (m, 2H), 1.81-1.87 (m, 2H), 2.01-2.04 (m, 4H), 2.66-2.69 (m, 2H), 3.12-3.14 (m, 2H), 3.46-3.59 (m, 4H), 3.87 (s, 3H), 7.00 (d, J = 8.6 Hz, 2H), 7.26 (d, J = 8.6 Hz, 2H): LC-MS (ESI) m/z 380 ([M + 1]⁺). |
| 1-77 | 4-MeO—Ph | —(CH₂)₄— | | cyclohexylmethyl-NH— | ¹H NMR (500 MHz, CDCl₃) δ 0.95 (dq, J = 3.0, 12.0 Hz, 2H), 1.12-1.27 (m, 3H), 1.55-1.59 (m, 2H), 1.62-1.79 (m, 8H), 1.82-1.86 (m, 2H), 2.66-2.68 (m, 2H), 3.11-3.24 (m, 2H), 3.25 (d, J = 6.3 Hz, 2H), 3.87 (s, 3H), 5.54 (br s, 1H), 6.99 (d, J = 8.7 Hz, 2H), 7.24 (d, J = 8.7 Hz, 2H): LC-MS (ESI) m/z 422 ([M + 1]⁺). |
| 1-78 | 4-MeO—Ph | —(CH₂)₄— | | 2-(piperidin-1-yl)ethyl-NH— | ¹H NMR (500 MHz, CDCl₃) δ 7.22 (d, J = 8.7 Hz, 2H), 6.98 (d, J = 8.7 Hz, 2H), 6.09 (br s, 1H), 3.87 (s, 3H), 3.57-3.50 (m, 2H), 3.18-3.11 (m, 2H), 2.71-2.64 (m, 2H), 2.62-2.55 (m, 2H), 2.50-2.35 (m, 4H), 1.89-1.80 (m, 2H), 1.78-1.72 (m, 2H), 1.62-1.53 (m, 6H), 1.48-1.40 (m, 2H): LC-MS (ESI) m/z 437 ([M + 1]⁺). |
| 1-79 | 4-MeO—Ph | —(CH₂)₄— | | 2-morpholinoethyl-NH— | ¹H NMR (500 MHz, CDCl₃) δ 7.24 (d, J = 8.7 Hz, 2H), 6.99 (d, J = 8.7 Hz, 2H), 5.83 (br s, 1H), 3.87 (s, 3H), 3.73-3.67 (t, J = 4.5 Hz, 4H), 3.58-3.52 (m, 2H), 3.16-3.11 (m, 2H), 2.72-2.66 (m, 2H), 2.65-2.60 (m, 2H), 2.48 (t, J = 4.5 Hz, 4H), 1.88-1.82 (m, 2H), 1.79-1.72 (m, 2H), 1.61-1.55 (m, 2H): LC-MS (ESI) m/z 439 ([M + 1]⁺). |
| 1-80 | 4-MeO—Ph | —(CH₂)₄— | | 2-(pyrrolidin-1-yl)ethyl-NH— | ¹H NMR (500 MHz, CDCl₃) δ 7.14 (d, J = 8.7 Hz, 2H), 6.96 (d, J = 8.7 Hz, 2H), 6.31 (br s, 1H), 3.87 (s, 3H), 3.60-3.55 (m, 2H), 3.17-3.11 (m, 2H), 2.78-2.72 (m, 2H), 2.69-2.63 (m, 2H), 2.57-2.52 (m, 4H), 1.86-1.80 (m, 2H), 1.80-1.72 (m, 6H), 1.59-1.53 (m, 2H): LC-MS (ESI) m/z 423 ([M + 1]⁺). |
| 1-81 | 4-MeO—Ph | —(CH₂)₄— | | 3-(pyrrolidin-1-yl)propyl-NH— | ¹H NMR (500 MHz, CDCl₃) δ 7.43 (br s, 1H), 7.24 (d, J = 8.8 Hz, 2H), 6.99 (d, J = 8.8 Hz, 2H), 3.87 (s, 3H), 3.59-3.53 (m, 2H), 3.15-3.09 (m, 2H), 2.70-2.60 (m, 4H), 2.56-2.47 (m, 4H), 1.88-1.71 (m, 10H), 1.60-1.54 (m, 2H): LC-MS (ESI) m/z 437 ([M + 1]⁺). |
| 1-82 | 4-MeO—Ph | Me | Me | BnNH— | ¹H NMR (500 MHz, CDCl₃) δ 1.37 (t, J = 7.5 Hz, 3H), 2.17 (s, 3H), 2.91 (q, J = 7.5 Hz, 2H), 3.87 (s, 3H), 4.69 (s, 2H), 5.48 (br s, 1H), 6.99 (d, J = 8.8 Hz, 2H), 7.26 (d, J = 8.8 Hz, 2H), 7.29 (m, 1H), 7.32-7.38 (m, 4H): LC-MS (ESI) m/z 390 ([M + 1]⁺). |
| 1-83 | 4-MeO—Ph | Me | Me | morpholino | ¹H NMR (500 MHz, CDCl₃) δ 1.35 (t, J = 7.5 Hz, 3H), 2.18 (s, 3H), 2.90 (q, J = 7.5 Hz, 2H), 3.62-3.65 (m, 4H), 3.76-3.80 (m, 4H), 3.87 (s, 3H), 7.01 (d, J = 8.8 Hz, 2H), 7.28 (d, J = 8.8 Hz, 2H): LC-MS (ESI) m/z 370 ([M + 1]⁺). |
| 1-84 | 4-MeO—Ph | Me | Me | piperidin-1-yl | ¹H NMR (500 MHz, CDCl₃) δ 1.34 (t, J = 7.5 Hz, 3H), 1.62-1.68 (m, 6H), 2.16 (s, 3H), 2.88 (q, J = 7.5 Hz, 2H), 3.63-3.69 (m, 4H), 3.87 (s, 3H), 6.74 (d, J = 8.8 Hz, 2H), 7.27 (d, J = 8.8 Hz, 2H): LC-MS (ESI) m/z 368 ([M + 1]⁺). |
| 1-85 | 4-MeO—Ph | Me | Me | 4-MeO—BnNH— | ¹H NMR (500 MHz, CDCl₃) δ 1.35 (t, J = 7.5 Hz, 3H), 2.17 (s, 3H), 2.90 (q, J = 7.5 Hz, 2H), 3.79 (s, 3H), 3.87 (S, 3H), 4.60 (s, 2H), 5.57 (br s, 1H), 6.86 (d, J = 8.5 Hz, 2H), 6.99 |

TABLE 1-continued

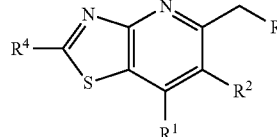

| No. | R¹ | R² | R³ | R⁴ | [¹H NMR (500 MHz, CDCl₃) δ LC/MS (ESI)] |
|---|---|---|---|---|---|
| | | | | | (d, J = 8.7 Hz, 2H), 7.26 (d, J = 8.7 Hz, 2H), 7.29 (d, J = 8.6 Hz, 2H): LC-MS (ESI) m/z 420 ([M + 1]⁺). |
| 1-86 | 4-MeO—Ph | Me | Me | n-PrNH— | ¹H NMR (500 MHz, CDCl₃) δ 0.97 (t, J = 7.4 Hz, 3H), 1.34 (t, J = 7.5 Hz, 3H), 1.70 (q, J = 7.3 Hz, 2H), 2.16 (s, 3H), 2.89 (q, J = 7.5 Hz, 2H), 3.39 (t, J = 7.0 Hz, 2H), 3.87 (s, 3H), 5.57 (br s, 1H), 7.00 (d, J = 8.7 Hz, 2H), 7.27 (d, J = 8.7 Hz, 2H): LC-MS (ESI) m/z 342 ([M + 1]⁺). |
| 1-87 | 4-MeO—Ph | Me | Me | 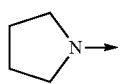 | ¹H NMR (500 MHz, CDCl₃) δ 1.35 (t, J = 7.5 Hz, 3H), 2.02-2.04 (m, 4H), 2.16 (s, 3H), 2.89 (q, J = 7.2 Hz, 2H), 3.45-3.62 (m, 4H), 3.87 (s, 3H), 7.00 (d, J = 8.7 Hz, 2H), 7.28 (d, J = 8.7 Hz, 2H): LC-MS (ESI): m/z 354 ([M + 1]⁺). |
| 1-88 | 4-MeO—Ph | Me | Me | 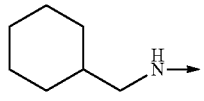 | ¹H NMR (500 MHz, CDCl₃) δ 0.95 (dq, J = 2.9, 12.1 Hz, 2H), 1.12-1.27 (m, 3H), 1.34 (t, J = 7.5 Hz, 3H), 1.63-1.68 (m, 2H), 1.70-1.79 (m, 4H), 2.16 (s, 3H), 2.89 (q, J = 7.5 Hz, 2H), 3.23 (s, 3H), 5.41 (br s, 1H), 7.00 (d, J = 8.7 Hz, 2H), 7.27 (d, J = 8.7 Hz, 2H): LC-MS (ESI) m/z 396 ([M + 1]⁺). |
| 1-89 | 4-NO₂—Ph | —(CH₂)₂— | | BnNH— | ¹H NMR (500 MHz, CDCl₃) δ 2.16 (tt, J = 7.5, 7.5 Hz, 2H), 2.90 (t, J = 7.3 Hz, 2H), 3.12 (t, J = 7.7 Hz, 2H), 4.68 (s, 2H), 5.77 (br s, 2H), 7.28-7.41 (m, 5H), 7.68 (d, J = 8.9 Hz, 2H), 8.35 (d, J = 8.9 Hz, 2H): LC-MS (ESI) m/z 402 ([M + 1]⁺). |
| 1-90 | 4-NO₂—Ph | —(CH₂)₂— | | 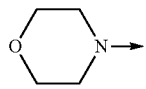 | ¹H NMR (500 MHz, CDCl₃) δ 2.16 (tt, J = 7.5, 7.5 Hz, 2H), 2.90 (t, J = 7.3 Hz, 2H), 3.10 (t, J = 7.6 Hz, 2H), 3.65-3.69 (m, 4H), 3.80-3.84 (m, 4H), 7.70 (d, J = 8.8 Hz, 2H), 8.36 (d, J = 8.8 Hz, 2H): LC-MS (ESI) m/z 383 ([M + 1]⁺). |
| 1-91 | 4-NO₂—Ph | —(CH₂)₂— | | 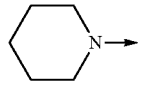 | ¹H NMR (500 MHz, CDCl₃) δ 2.02-2.07 (m, 6H), 2.48 (m, 2H), 3.29 (t, J = 7.3, 2H), 3.44 (t, J = 7.7, 2H), 3.96-4.00 (m, 4H), 8.04 (d, J = 8.9 Hz, 2H), 8.69 (d, J = 8.9 Hz, 2H): LC-MS (ESI) m/z 381 ([M + 1]⁺). |
| 1-92 | 4-NO₂—Ph | —(CH₂)₂— | | 4-MeO—BnNH— | ¹H NMR (500 MHz, CDCl₃) δ 2.16 (m, 2H), 2.90 (t, J = 7.5 2H), 3.13 (t, J = 7.6 Hz, 2H), 3.80 (s, 3H), 4.61 (s, 2H), 5.61 (br s, 1H), 6.88 (d, J = 8.7 Hz, 2H), 7.31 (d, J = 8.6 Hz, 2H), 7.68 (d, J = 8.8 Hz, 2H), 8.35 (d, J = 8.8 Hz, 2H): LC-MS (ESI) m/z 433 ([M + 1]⁺). |
| 1-93 | 4-NO₂—Ph | —(CH₂)₂— | | n-PrNH— | ¹H NMR (500 MHz, CDCl₃) δ 0.99 (t, J = 7.4 Hz, 3H), 1.73 (q, J = 7.3 Hz, 2H), 2.15 (m, 2H), 2.89 (t, J = 7.3 Hz, 2H), 3.10 (t, J = 7.6 Hz, 2H), 3.40 (t, J = 7.1 Hz, 2H), 5.81 (br s, 1H), 7.69 (d, J = 6.9 Hz, 2H), 8.35 (d, J = 8.9 Hz, 2H): LC-MS (ESI) m/z 355 ([M + 1]⁺). |
| 1-94 | 4-NO₂—Ph | —(CH₂)₂— | | 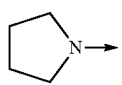 | ¹H NMR (500 MHz, CDCl₃) δ 2.05-2.09 (m, 4H), 2.15 (m, 2H), 2.89 (t, J = 7.3 Hz, 2H), 3.10 (t, J = 7.6 Hz, 2H), 3.50-3.67 (m, 4H), 7.71 (d, J = 8.6 Hz, 2H), 8.36 (d, J = 8.6 Hz, 2H): LC-MS (ESI) m/z 367 ([M + 1]⁺). |
| 1-95 | 4-NO₂—Ph | —(CH₂)₂— | | 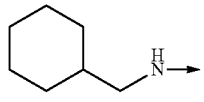 | ¹H NMR (500 MHz, CDCl₃) δ 0.98 (dq, J = 3.1, 12.0 Hz, 2H), 1.14-1.28 (m, 3H), 1.66-1.81 (m, 6H), 2.14 (m, 2H), 2.89 (t, J = 7.3 Hz, 2H), 3.11 (t, J = 7.6 Hz, 2H), 3.27 (d, J = 5.4 Hz, 2H), 5.66 (br s, 1H), 7.69 (d, J = 8.9 Hz, 2H), 8.36 (d, J = 8.9 Hz, 2H): LC-MS (ESI) m/z 409 ([M + 1]⁺). |
| 1-96 | 4-NO₂—Ph | —(CH₂)₃— | | BnNH— | ¹H NMR (500 MHz, CDCl₃) δ 1.73-1.78 (m, 2H), 1.88-1.94 (m, 2H), 2.50 (t, J = 6.3 Hz, 2H), 3.05 (t, J = 6.5 Hz, 2H), 4.68 (s, 2H), 5.73 (br s, 1H), 7.27-7.39 (m, 5H), 7.52 (d, J = 8.7 Hz, 2H), 8.34 (d, J = 8.7 Hz, 2H): LC-MS (ESI) m/z 417 ([M + 1]⁺). |
| 1-97 | 4-NO₂—Ph | —(CH₂)₃— | | 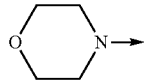 | ¹H NMR (500 MHz, CDCl₃) δ 1.73-1.77 (m, 2H), 1.88-1.92 (m, 2H), 2.51 (t, J = 6.3 Hz, 2H), 3.05 (t, J = 6.6 Hz, 2H), 3.63-3.66 (m, 4H), 3.77-3.81 (m, 4H), 7.54 (d, J = 8.9 Hz, 2H), 8.35 (d, J = 8.9 Hz, 2H): LC-MS (ESI) m/z 397 ([M + 1]⁺). |

TABLE 1-continued

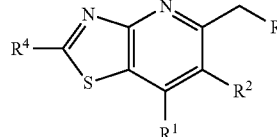

[화학식1]

| 화합물 | R¹ | R² | R³ | R⁴ | 분석자료[¹H NMR (500 MHz, CDCl₃) δ LC/MS (ESI)] |
|---|---|---|---|---|---|
| 1-98 | 4-NO₂—Ph | —(CH₂)₃— | | 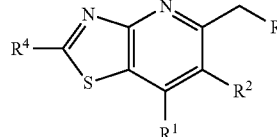 | ¹H NMR (500 MHz, CDCl₃) δ 1.62-1.69 (m, 6H), 1.71-1.77 (m, 2H), 1.87-1.92 (m, 2H), 2.49 (t, J = 6.3 Hz, 2H), 3.03 (t, J = 6.6, 2H), 3.58-3.63 (m, 4H), 7.53 (d, J = 8.8 Hz, 2H), 8.34 (d, J = 8.8 Hz, 2H): LC-MS (ESI) m/z 395 ([M + 1]⁺). |
| 1-99 | 4-NO₂—Ph | —(CH₂)₃— | | 4-MeO—BnNH— | ¹H NMR (500 MHz, CDCl₃) δ 1.72-1.78 (m, 2H), 1.88-1.93 (m, 2H), 2.50 (t, J = 6.3 Hz, 2H), 3.05 (t, J = 6.6, 2H), 3.79 (s, 3H), 4.60 (s, 2H), 5.69 (br s, 1H), 6.86 (d, J = 8.7 Hz, 2H), 7.29 (d, J = 8.6 Hz, 2H), 7.52 (d, J = 8.8 Hz, 2H), 8.34 (d, J = 8.8 Hz, 2H): LC-MS (ESI) m/z 447 ([M + 1]⁺). |
| 1-100 | 4-NO₂—Ph | —(CH₂)₂— | | n-PrNH— | ¹H NMR (500 MHz, CDCl₃) δ 0.97 (t, J = 7.4 Hz, 3H), 1.71 (q, J = 6.4 Hz, 2H), 1.73-1.78 (m, 2H), 1.87-1.93 (m, 2H), 2.49 (t, J = 6.3 Hz, 2H), 3.04 (t, J = 6.6 Hz, 2H), 3.40 (t, J = 7.0 Hz, 2H), 5.61 (br s, 1H), 7.53 (d, J = 8.8 Hz, 2H), 8.35 (d, J = 8.8 Hz, 2H): LC-MS (ESI) m/z 369 ([M + 1]⁺). |
| 1-101 | 4-NO₂—Ph | —(CH₂)₃— | | 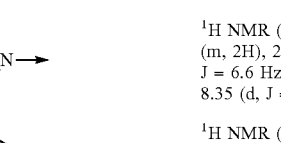 | ¹H NMR (500 MHz, CDCl₃) δ 1.72-1.77 (m, 2H), 1.86-1.92 (m, 2H), 2.03-2.07 (m, 4H), 2.50 (t, J = 6.3 Hz, 2H), 3.04 (t, J = 6.6 Hz, 2H), 3.42-3.64 (m, 4H), 7.54 (d, J = 8.8 Hz, 2H), 8.35 (d, J = 8.8 Hz, 2H): LC-MS (ESI) m/z 381 ([M + 1]⁺). |
| 1-102 | 4-NO₂—Ph | —(CH₂)₃— | | 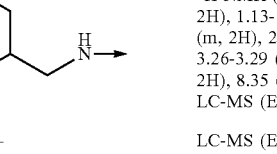 | ¹H NMR (500 MHz, CDCl₃) δ 0.96 (dq, J = 2.9, 12.0 Hz, 2H), 1.13-1.27 (m, 3H), 1.64-1.80 (m, 8H), 1.87-1.92 (m, 2H), 2.49 (t, J = 6.3 Hz, 2H), 3.04 (t, J = 6.6 Hz, 2H), 3.26-3.29 (m, 2H), 5.51 (br s, 1H), 7.53 (d, J = 8.8 Hz, 2H), 8.35 (d, J = 8.9 Hz, 2H): LC-MS (ESI) m/z 423 ([M + 1]⁺). |
| 1-103 | 3-NO₂—Ph | —(CH₂)₃— | | BnNH— | LC-MS (ESI) m/z 417 ([M + 1]⁺). |
| 1-104 | 4-Me—Ph | —(CH₂)₃— | | BnNH— | LC-MS (ESI) m/z 386 ([M + 1]⁺). |
| 1-105 | 4-Me—Ph | —(CH₂)₃— | | BnNH— | LC-MS (ESI) m/z 386 ([M + 1]⁺). |
| 1-106 | 4-F—Ph | —(CH₂)₃— | | BnNH— | LC-MS (ESI) m/z 390 ([M + 1]⁺). |
| 1-107 | 3-F—Ph | —(CH₂)₃— | | BnNH— | LC-MS (ESI) m/z 390 ([M + 1]⁺). |
| 1-108 | 4-Cl—Ph | —(CH₂)₃— | | BnNH— | LC-MS (ESI) m/z 406 ([M + 1]⁺). |
| 1-109 | 3-Cl—Ph | —(CH₂)₃— | | BnNH— | LC-MS (ESI) m/z 406 ([M + 1]⁺). |
| 1-110 | 4-Ph—Ph | —(CH₂)₃— | | BnNH— | LC-MS (ESI) m/z 448 ([M + 1]⁺). |

Example 3. Confirmation of Effect of Inhibiting Permeability of Vein Endothelial Cells Induced by HMGB1

A polyester membrane having a pore of 3 μm and a diameter of 12 mm was coated in a 0.2% gelatin solution for 2 hours, washed with deionized water, and natural-dried at room temperature.

Meanwhile, human umbilical vein endothelial cells (HUVECs) cultured in a complete EBM-2 medium including a 10% fetal bovine serum were harvested using a trypsin/EDTA solution, and dispensed into an upper chamber of each well at $5 \times 10^4/500$ μl, and 1.5 ml of the EBM-2 medium was added into a lower chamber, and the cells were cultured in a $CO_2$ incubator at 37° C. for 3 days. The HUVECs having a density of approximately 90% were cultured in the prepared compounds at a concentration of 100 nM for 3 hours, and the upper chamber was washed with PBS and treated with HMGB1 (1 μg/ml) for 16 hours. The lower chamber of each well of a plate was filled with 1.5 ml of the EBM-2 medium, the upper chamber was washed with PBS, 500 μl of a reagent prepared by mixing an Evansblue dye (0.67 mg/ml), 40% BSA and a 60% fresh medium was put into each chamber, and after 10 minutes, the medium of the lower chamber was confirmed at 650 nm.

A permeability inhibition ratio of the vein endothelial cell was calculated according to Equation 1, and the result is shown in Table 2.

$$\% \text{ Inhibition Ratio (\%)} = \frac{(HMGB1 \text{ only treatment group} - testdrug \text{ treatment group})}{(HMGB1 \text{ only treatment group} - HMGB1 \text{ non-treatment group})} \times 100 \quad \text{[Equation 1]}$$

TABLE 2

| 화합물 번호 (100 μM) | Inhibition (%) |
|---|---|
| 대조군 | 100 |
| HMGB1 | 0 |
| 1-2 | −16.05 |
| 1-11 | −2.13 |
| 1-12 | −31.91 |
| 1-19 | 59.77 |
| 1-20 | 61.32 |

TABLE 2-continued

| (100 μM) | Inhibition (%) |
|---|---|
| 1-22 | 77.37 |
| 1-23 | 28.63 |
| 1-35 | 77.76 |
| 1-36 | 88.97 |
| 1-39 | 76.40 |
| 1-49 | 85.49 |
| 1-50 | 68.47 |
| 1-57 | −26.31 |
| 1-62 | 92.65 |
| 1-63 | 93.81 |
| 1-64 | 86.85 |
| 1-65 | 97.29 |
| 1-66 | 98.07 |
| 1-68 | −64.02 |
| 1-69 | 62.86 |
| 1-74 | 75.24 |
| 1-75 | 88.78 |
| 1-85 | −3.29 |
| 1-86 | −10.25 |
| 1-87 | −6.19 |
| 1-92 | 71.76 |
| 1-93 | 77.37 |
| 1-97 | 83.56 |
| 1-99 | 81.82 |
| 1-100 | 33.08 |
| 1-101 | 89.75 |

As shown in Table 2, it was confirmed that Compounds 1-65 and 1-66 exhibited an inhibitory effect of 97.29% and 98.07%, respectively, and the HMGB1-induced permeability of the vein endothelial cells for other compounds was strongly inhibited. This shows that amplification of an immune reaction to an antigen penetrated from an external environment can be regulated by inhibiting a vein barrier protection effect and attachment and transfer of immune cells to the vein endothelial cells in vivo.

Example 4. Confirmation of Increase in Survival Rate of Sepsis Mouse Model Induced by CLP An anti-inflammation effect of the prepared compound was tested by a survival rate of the sepsis mouse model induced by peritonitis. A CLP-induced sepsis mouse model is an in vivo method for investigating an anti-inflammation action, and the manufacturing method of the mouse model is a widely used experiment method [Wang H, Nat. Med., 2004, 10, 1216-1221]. 40 six-week-old male ICR mice were divided into 10 mice per each group, and the survival rate was observed.

First, after the male mouse was anesthetized by respiration using isoflurane, the abdomen of the mouse was cut in the middle by approximately 2 cm to take out an appendix adjacent to intestines, and the appendix was tied up at a part apart from 0.5 mm from the end of the appendix with a 3.0-silk suture, pierced once with a 22-gauge needle, and sutured the cut part with a 4.0 silk suture. An abdomen of a sham mouse was cut and sutured without tie-up or piercing of the appendix, and after 12 and 50 hours of the surgery, the prepared compound was administered by mouse tail intravenous injection. At every 6 hours after the surgery, the survival rate of the mouse was observed, and the result is shown in FIG. 1.

As shown in FIG. 1, it was confirmed that in the 1-65 compound, the survival rate of the CLP-induced sepsis mouse model was increased 60%, compared to the only CLP-treated group, and other compounds showed the survival rate of approximately 40%. Such a result equaled to an effect of activated protein A approved by FDA to improve the survival rate of the sepsis mouse model. According to the experiment result, an anti-inflammation effect for a vascular inflammatory disease of the 2,5,6,7-tetrasubstituted thiazolo[4,5-b]pyridine derivative was confirmed.

PREPARATION EXAMPLES

Preparation Example 1. Preparation of Tablet (Pressing)

A tablet was prepared by sieving 5.0 mg of the compound represented by Formula 1 of the present invention as an active ingredient, mixing 14.1 mg of a lactose, 0.8 mg of crospovidone USNF and 0.1 mg of magnesium stearate, and pressing the resulting product.

Preparation Example 2. Preparation of Tablet (Wet Assembly)

As an active ingredient, 5.0 mg of the compound represented by Formula 1 of the present invention was sieved, and 16.0 mg of a lactose and 4.0 mg of starch were mixed. 0.3 mg of polysorbate 80 was dissolved in pure water, a suitable amount of the solution was added to the above mixture, and then the resulting mixture was atomized. After drying, the resulting fine particles were sieved, and 2.7 mg of colloidal silicon dioxide and 2.0 mg of magnesium stearate were mixed. The fine particles were pressed to prepare a tablet.

Preparation Example 3. Preparation of Powder and Capsule

As an active ingredient, 5.0 mg of the compound represented by Formula 1 of the present invention was sieved, and 14.8 mg of a lactose, 10.0 mg of polyvinyl pyrrolidone and 0.2 mg of magnesium stearate were mixed together. The resulting mixture was filled in a rigid No. 5 gelatin capsule using a suitable apparatus.

Preparation Example 4. Preparation of Injection

An injection was prepared by containing 100 mg of the compound represented by Formula 1 of the present invention as an active ingredient and containing 180 mg of mannitol, 26 mg of $Na_2HPO_4 12H_2O$ and 2,974 mg of distilled water.

The present invention provides a 2,5,6,7-tetrasubstituted thiazolo[4,5-b]pyridine derivative and a pharmaceutically available salt thereof, which are expected to be used in preventing or treating a vascular inflammatory disease and infectious disease including sepsis through an inhibitory effect of activity of HMGB1 protein of the compound by identifying HMGB1 protein activity inhibitory effect of the derivative and excellent inhibitory activity through a CLP-induced sepsis animal test.

While the present invention has been shown and described with reference to certain exemplary embodiments thereof, it will be understood by those skilled in the related art that various changes in form and details may be made therein without departing from the gist and scope of the present invention as defined by the appended claims.

What is claimed is:

1. A method of inhibiting activity of HMGB1 protein, comprising:

contacting HMGB1 protein with a 2,5,6,7-tetrasubstituted thiazolo[4,5-b]pyridine derivative represented by Formula 1 or a pharmaceutically available salt thereof,

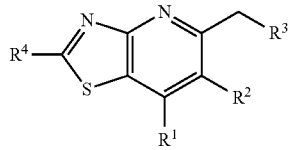

[Formula 1]

where $R^1$ is a five to seven-membered substituted or unsubstituted aromatic group to which carbon, oxygen, nitrogen or sulfur is added, in which the aromatic group is a heteroaryl group, a phenyl group or a substituted phenyl group, here, the substituent is one to four substituents selected from the group consisting of hydrogen, halogen, cyano, nitro, hydroxy, $C_1$-$C_{10}$ linear or branched alkyl, $C_1$-$C_{10}$ alkoxy, $C_1$-$C_{10}$ haloalkyl, $C_1$-$C_{10}$ haloalkoxy, $C_1$-$C_{10}$ alkylthio, $C_1$-$C_{10}$ alkyl carbonyl and a $C_1$-$C_{10}$ alkoxy carbonyl group, $R^2$ and $R^3$ are hydrogen, a $C_1$-$C_{10}$ linear, branched or cyclic alkyl group, a cyclic $C_1$-$C_{10}$ alkyl group including a heteroelement (—S— or —O—) or heteroalkyl group, or a $C_1$-$C_{10}$ linear or branched carbonyl group, which are independently or identically substituted, $R^4$ is an amino group substituted by one or at least two $C_1$-$C_{10}$ linear, branched or cyclic alkyl groups, $C_5$-$C_{10}$ aryl groups, $C_5$-$C_{10}$ heteroaryl groups or substituted heteroaryl groups, $C_5$-$C_{10}$ arylalkyl groups, a benzyl group, a substituted benzyl group or $C_5$-$C_{10}$ heteroarylalkyl groups, or a phenyl group, a substituted phenyl group, a benzyl group, a substituted benzyl group, a $C_1$-$C_{10}$ linear, branched or cyclic alkyl group, or an amine group having a piperazine

substituted by phenyl or a heteroarylamide group, or $C_3$-$C_{10}$ cyclic amine groups, or $C_3$-$C_{10}$ cyclic amine groups containing at least one heteroatom selected from the group consisting of N, O, and S, here, the substituent is one to three substituents selected from the group consisting of a halogen atom, a nitro group, a $C_1$-$C_{10}$ alkyl group, a $C_1$-$C_{10}$ alkoxy group, a $C_1$-$C_{10}$ haloalkyl group and a $C_1$-$C_{10}$ haloalkoxy group.

2. A method of inhibiting activity of HMGB1 protein, comprising:
contacting HMGB1 protein with a 2,5,6,7-tetrasubstituted thiazolo[4,5-b]pyridine derivative represented by Formula 1 or a pharmaceutically available salt thereof,

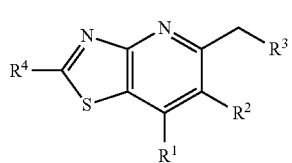

[Formula 1]

wherein, in Formula 1, $R^1$ is a five to seven-membered substituted or unsubstituted aromatic group to which carbon, oxygen, nitrogen or sulfur is added, in which the aromatic group is a furanyl group, a thiophenyl group, a phenyl group, a thiazole group, an indole group, an isoindole group, a pyridinyl group, a piperazinyl group, a pyridazinyl group, a naphthyl group, a quinolinyl group, or an isoquinolinyl group, here, the substituent includes one to three substituents selected from the group consisting of hydrogen, halogen, cyano, nitro, hydroxy, $C_1$-$C_6$ linear or branched alkyl, $C_1$-$C_6$ alkoxy, $C_1$-$C_6$ haloalkyl, $C_1$-$C_6$ haloalkoxy, $C_1$-$C_6$ alkylthio, $C_1$-$C_6$ alkyl carbonyl and a $C_1$-$C_6$ alkoxy carbonyl group, $R^2$ and $R^3$ are hydrogen, a $C_1$-$C_6$ linear, branched or cyclic alkyl group, a cyclic $C_1$-$C_6$ alkyl group including a heteroelement (—NH—, —S—, —O—) or heteroalkyl group, or a $C_1$-$C_6$ linear or branched carbonyl group, which are independently or identically substituted, and $R^4$ is an amino group substituted by one or at least two $C_1$-$C_6$ linear, branched or cyclic alkyl groups, $C_5$-$C_6$ aryl groups, $C_5$-$C_6$ heteroaryl groups or substituted heteroaryl groups, $C_5$-$C_6$ arylalkyl groups, a benzyl group, a substituted benzyl group or $C_5$-$C_6$ heteroarylalkyl groups, or a phenyl group, a substituted phenyl group, a benzyl group, a substituted benzyl group, a $C_1$-$C_6$ linear, branched or cyclic alkyl group, or an amine group having a piperazine

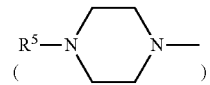

substituted by phenyl or a heteroarylamide group, or a $C_3$-$C_6$ cyclic amine group, or a $C_3$-$C_6$ cyclic amine groups containing at least one heteroatom selected from the group consisting of N, O, and S, here, the substituent is one to three substituents selected from the group consisting of a halogen atom, a nitro group, a $C_1$-$C_6$ alkyl group, a $C_1$-$C_6$ alkoxy group, a $C_1$-$C_6$ haloalkyl group and a $C_1$-$C_6$ haloalkoxy group.

3. The method according to claim 2, wherein, in Formula 1, $R^1$ is a phenyl group, a substituted phenyl group, an aryl group, or a substituted aryl group, in which the aryl group is a furanyl group, a thiophenyl group, a thiazole group, an indole group, an isoindole group, a pyridinyl group, a piperazinyl group, a pyridazinyl group, a naphthyl group, a quinolinyl group, an isoquinolinyl group, here, the substituent includes one to three substituents selected from the group consisting of hydrogen, chloro, fluoro, a hydroxyl group, a cyano group, a nitro group, a methyl group, an ethyl group, an isopropyl group, a cyclopropyl group, a t-butyl group, a methoxy group, an ethoxy group, an n-propoxy group, an isopropoxy group, a thiomethoxy group, a thioethoxy group, a thio n-propoxy group, a thio isopropoxy group, a trifluoromethoxy group, a trifluoromethyl group, a methylester group, and an ethylester group, $R^2$ and $R^3$ are independently hydrogen, methyl, ethyl, n-propyl, butyl, an isopropyl group, or identically cyclopentyl, cyclohexyl, cycloheptyl, cyclopentanone, cyclohexanone, cycloheptanone, tetrahydropyran, tetrahydrothiopyran or piperidine, and $R^4$ is an amino group substituted by one or at least two $C_1$-$C_6$ linear, branched or cyclic alkyl groups, $C_5$-$C_6$ aryl groups, $C_5$-$C_6$ heteroaryl groups or substituted heteroaryl groups, $C_5$-$C_6$ arylalkyl groups, a benzyl group or $C_5$-$C_6$ heteroarylalkyl groups, or a phenyl group, a substituted phenyl group, a benzyl group, a substituted benzyl group, a $C_1$-$C_{10}$ linear, branched or cyclic alkyl group, or a $C_3$-$C_6$ cyclic amine group, or a $C_3$-$C_6$ cyclic amine groups containing at least one heteroatom selected from the group consisting of N, O, and S, here, the substituent is one to three substituents selected from the group consisting of a halogen atom, a nitro group, a $C_1$-$C_4$ alkyl group, a $C_1$-$C_4$ alkoxy group, a $C_1$-$C_3$ haloalkyl group and a $C_1$-$C_3$ haloalkoxy group.

\* \* \* \* \*